US012357777B2

(12) United States Patent
Buchberger et al.

(10) Patent No.: US 12,357,777 B2
(45) Date of Patent: *Jul. 15, 2025

(54) AEROSOL PROVISION SYSTEMS

(71) Applicant: NICOVENTURES TRADING LIMITED, London (GB)

(72) Inventors: Helmut Buchberger, Florian (AT); David Leadley, London (GB)

(73) Assignee: Nicoventures Trading Limited, London (GB)

( * ) Notice: Subject to any disclaimer, the term of this patent is extended or adjusted under 35 U.S.C. 154(b) by 944 days.

This patent is subject to a terminal disclaimer.

(21) Appl. No.: 17/305,226

(22) Filed: Jul. 1, 2021

(65) Prior Publication Data
US 2021/0322687 A1 Oct. 21, 2021

Related U.S. Application Data

(63) Continuation of application No. 15/533,296, filed as application No. PCT/GB2015/053445 on Nov. 13, 2015, now Pat. No. 11,083,856.

(30) Foreign Application Priority Data

Dec. 11, 2014 (GB) .................... 1422018

(51) Int. Cl.
A61M 15/06 (2006.01)
A24F 40/10 (2020.01)
(Continued)

(52) U.S. Cl.
CPC .......... A61M 15/06 (2013.01); A24F 40/485 (2020.01); A61M 11/042 (2014.02);
(Continued)

(58) Field of Classification Search
CPC ........ A61M 11/042; A61M 2205/3368; A61M 2205/3653; A61M 2205/8206; A24F 40/10; A24F 40/46
See application file for complete search history.

(56) References Cited

U.S. PATENT DOCUMENTS 228,598 A 6/1880 Buckley
353,327 A 11/1886 Randolph
(Continued)

FOREIGN PATENT DOCUMENTS

AT 507187 A4 3/2010
AT 507187 B1 3/2010
(Continued)

OTHER PUBLICATIONS

Aerosols, "Pulmonary Pharmacology: Delivery Devices and Medications," Sep. 6, 2017, available at www.cdeu.org/cecourses/z98207/ch4.html, 2 pages.
(Continued)

Primary Examiner — Kathryn E Ditmer
(74) Attorney, Agent, or Firm — Merchant & Gould P.C.

(57) ABSTRACT

An apparatus for an electronic aerosol provision system may include a replaceable cartridge for the electronic aerosol provision system or a fixed component of a re-fillable or disposable electronic aerosol provision system. The apparatus includes a reservoir for a source liquid and a carrier module supported within the reservoir. The carrier module defines an airflow path within the reservoir and includes a heating element supported in the airflow path for generating an aerosol from the source liquid and first and second mounting parts which cooperatively engage to support the heating element. The first and second mounting parts cooperatively engage at an interface which extends in a direction substantially parallel to a direction along which air flows in the airflow path when the apparatus is in normal use. A gap
(Continued)

between the first and second mounting parts may provide a capillary channel for drawing source liquid to the heating element from the reservoir heating during use.

17 Claims, 7 Drawing Sheets

(51) Int. Cl.
    *A24F 40/485*     (2020.01)
    *A61M 11/04*     (2006.01)

(52) U.S. Cl.
    CPC ............ *A61M 11/044* (2014.02); *A24F 40/10* (2020.01); *A61M 2205/3368* (2013.01); *A61M 2205/3653* (2013.01); *A61M 2205/8206* (2013.01)

(56) References Cited

U.S. PATENT DOCUMENTS

| | | | |
|---|---|---|---|
| 576,653 A | 2/1897 | Bowlby | |
| 595,070 A | 12/1897 | Oldenbusch | |
| 744,074 A | 11/1903 | Hiering | |
| 799,844 A | 9/1905 | Fuller | |
| 885,374 A | 4/1908 | Pohlig | |
| 1,163,183 A | 12/1915 | Stoll | |
| D53,386 S | 5/1919 | Thomas | |
| 1,436,157 A | 11/1922 | Fazio | |
| 1,807,936 A | 6/1931 | Saunders | |
| 1,815,069 A | 7/1931 | Petro | |
| 1,937,120 A | 11/1933 | Julius et al. | |
| 1,937,987 A | 12/1933 | Sexton | |
| 2,057,353 A | 10/1936 | Whittemore | |
| 2,262,318 A | 11/1941 | Fox | |
| 2,371,006 A | 3/1945 | Weaver | |
| 2,411,946 A | 12/1946 | Max et al. | |
| 2,467,923 A | 4/1949 | Allen | |
| 2,483,304 A | 9/1949 | Rudolf et al. | |
| 2,522,952 A | 9/1950 | Joseph et al. | |
| 2,658,368 A | 11/1953 | Siegel | |
| 2,782,910 A | 2/1957 | Saul et al. | |
| 2,809,634 A | 10/1957 | Hirotada et al. | |
| 3,111,396 A | 11/1963 | Ball | |
| 3,165,225 A | 1/1965 | Georg et al. | |
| 3,402,724 A | 9/1968 | Blount et al. | |
| 3,431,393 A | 3/1969 | Katsuda et al. | |
| 3,433,632 A | 3/1969 | Elbert et al. | |
| 3,490,718 A | 1/1970 | Vary et al. | |
| 3,496,336 A | 2/1970 | Hingorany et al. | |
| 3,521,643 A | 7/1970 | Toth et al. | |
| 3,604,428 A | 9/1971 | Moukaddem | |
| 3,722,742 A | 3/1973 | Wertz | |
| 3,743,136 A | 7/1973 | Chambers | |
| 3,804,100 A | 4/1974 | Fariello | |
| 3,861,523 A | 1/1975 | Fountain et al. | |
| 3,863,803 A | 2/1975 | Valcic | |
| 3,964,902 A | 6/1976 | Fletcher et al. | |
| 4,009,713 A | 3/1977 | Simmons et al. | |
| 4,031,906 A | 6/1977 | Knapp | |
| 4,094,119 A | 6/1978 | Sullivan | |
| 4,145,001 A | 3/1979 | Weyenberg et al. | |
| 4,161,282 A * | 7/1979 | Erb .................... | B05B 7/0416 |
| | | | 128/200.14 |
| 4,161,283 A | 7/1979 | Hyman | |
| 4,190,412 A | 2/1980 | Nitta | |
| 4,193,513 A | 3/1980 | Bull, Jr. | |
| 4,214,658 A | 7/1980 | Crow | |
| 4,449,039 A | 5/1984 | Fukazawa et al. | |
| 4,503,851 A | 3/1985 | Braunroth | |
| D279,508 S | 7/1985 | Bauer et al. | |
| 4,588,976 A | 5/1986 | Jaselli | |
| 4,676,237 A | 6/1987 | Wood et al. | |
| 4,677,992 A | 7/1987 | Bliznak | |
| 4,733,794 A | 3/1988 | Kent | |
| 4,735,217 A | 4/1988 | Gerth et al. | |
| 4,753,383 A | 6/1988 | Focke et al. | |
| 4,793,478 A | 12/1988 | Tudor | |
| 4,830,028 A | 5/1989 | Lawson et al. | |
| 4,848,374 A | 7/1989 | Chard et al. | |
| 4,878,832 A | 11/1989 | Lynch | |
| 4,885,129 A | 12/1989 | Leonard et al. | |
| 4,917,301 A | 4/1990 | Munteanu | |
| 4,922,901 A | 5/1990 | Brooks et al. | |
| 4,923,052 A | 5/1990 | Englebert | |
| 4,923,059 A | 5/1990 | Evers et al. | |
| 4,947,874 A | 8/1990 | Brooks et al. | |
| 4,947,875 A | 8/1990 | Brooks et al. | |
| 4,961,438 A | 10/1990 | Korte | |
| 4,978,814 A | 12/1990 | Honour | |
| 5,027,837 A | 7/1991 | Clearman et al. | |
| 5,044,550 A | 9/1991 | Lamm | |
| 5,046,514 A | 9/1991 | Bolt | |
| 5,060,671 A | 10/1991 | Counts et al. | |
| D322,687 S | 12/1991 | Tschudin | |
| 5,095,647 A | 3/1992 | Zobele et al. | |
| 5,095,921 A | 3/1992 | Losee et al. | |
| 5,096,921 A | 3/1992 | Bollinger et al. | |
| 5,099,861 A | 3/1992 | Clearman et al. | |
| 5,121,881 A | 6/1992 | Lembeck | |
| 5,167,242 A | 12/1992 | Turner et al. | |
| 5,179,966 A | 1/1993 | Losee et al. | |
| 5,247,947 A | 9/1993 | Clearman et al. | |
| 5,269,327 A | 12/1993 | Counts et al. | |
| D346,878 S | 5/1994 | Gee et al. | |
| 5,322,075 A | 6/1994 | Deevi et al. | |
| 5,357,271 A | 10/1994 | Wiklof et al. | |
| 5,388,574 A | 2/1995 | Ingebrethsen | |
| 5,390,864 A | 2/1995 | Alexander | |
| 5,404,890 A | 4/1995 | Gentry et al. | |
| 5,408,574 A | 4/1995 | Deevi et al. | |
| 5,448,317 A | 9/1995 | Huang | |
| 5,479,948 A | 1/1996 | Counts et al. | |
| 5,497,792 A | 3/1996 | Prasad et al. | |
| 5,501,236 A | 3/1996 | Hill et al. | |
| 5,505,214 A | 4/1996 | Collins et al. | |
| 5,530,225 A | 6/1996 | Hajaligol | |
| 5,540,241 A | 7/1996 | Kim | |
| 5,553,791 A | 9/1996 | Alexander | |
| 5,568,819 A | 10/1996 | Gentry et al. | |
| 5,636,787 A | 6/1997 | Gowhari | |
| 5,649,554 A | 7/1997 | Sprinkel et al. | |
| 5,659,656 A | 8/1997 | Das | |
| 5,666,977 A | 9/1997 | Higgins et al. | |
| 5,692,291 A | 12/1997 | Deevi et al. | |
| D392,069 S | 3/1998 | Rowland | |
| 5,743,251 A | 4/1998 | Howell et al. | |
| D404,201 S | 1/1999 | Wennerstrom | |
| 5,865,185 A | 2/1999 | Collins et al. | |
| 5,875,968 A | 3/1999 | Miller et al. | |
| 5,878,722 A | 3/1999 | Gras et al. | |
| 5,878,752 A | 3/1999 | Adams et al. | |
| 5,896,984 A | 4/1999 | Focke et al. | |
| D414,892 S | 10/1999 | Chen | |
| 5,967,312 A | 10/1999 | Jacobs | |
| 6,040,560 A | 3/2000 | Fleischhauer et al. | |
| 6,058,711 A | 5/2000 | Maciaszek et al. | |
| 6,065,592 A | 5/2000 | Wik | |
| 6,095,505 A | 8/2000 | Miller | |
| D432,263 S | 10/2000 | Issa | |
| D434,217 S | 11/2000 | Packard et al. | |
| D434,979 S | 12/2000 | Liu | |
| 6,155,268 A | 12/2000 | Takeuchi | |
| D436,725 S | 1/2001 | Rogers | |
| D438,003 S | 2/2001 | Minagawa et al. | |
| D441,133 S | 4/2001 | Emery | |
| 6,275,650 B1 | 8/2001 | Lambert | |
| D449,521 S | 10/2001 | Pinkus et al. | |
| 6,321,757 B1 | 11/2001 | McCutcheon | |
| 6,446,793 B1 | 9/2002 | Layshock | |
| D466,012 S | 11/2002 | Baker | |
| D470,765 S | 2/2003 | Baker | |
| D471,804 S | 3/2003 | Staples | |
| D472,012 S | 3/2003 | South | |

(56) References Cited

U.S. PATENT DOCUMENTS

| | | |
|---|---|---|
| 6,527,166 B1 | 3/2003 | Focke et al. |
| 6,530,495 B1 | 3/2003 | Joseph |
| 6,561,391 B1 | 5/2003 | Baker |
| 6,652,804 B1 | 11/2003 | Neumann et al. |
| 6,681,998 B2 | 1/2004 | Sharpe et al. |
| 6,701,921 B2 | 3/2004 | Sprinkel, Jr. et al. |
| 6,715,605 B1 | 4/2004 | Manservigi et al. |
| D493,617 S | 8/2004 | Armato |
| 6,790,496 B1 | 9/2004 | Levander et al. |
| 6,830,046 B2 | 12/2004 | Blakley et al. |
| D509,732 S | 9/2005 | Staples |
| 7,100,618 B2 | 9/2006 | Dominguez |
| 7,112,712 B1 | 9/2006 | Ancell |
| D545,186 S | 6/2007 | Liebe et al. |
| D549,573 S | 8/2007 | Liebe et al. |
| 7,253,282 B2 | 8/2007 | Dehmlow et al. |
| 7,263,228 B2 | 8/2007 | Mori |
| 7,263,282 B2 | 8/2007 | Meyer |
| D550,455 S | 9/2007 | Barnhart |
| D566,329 S | 4/2008 | Bagaric et al. |
| D566,890 S | 4/2008 | Bagaric et al. |
| 7,389,878 B1 | 6/2008 | Torrico |
| D573,889 S | 7/2008 | Short et al. |
| 7,400,940 B2 | 7/2008 | McRae et al. |
| D575,451 S | 8/2008 | Jones et al. |
| 7,455,176 B2 | 11/2008 | Focke et al. |
| 7,540,286 B2 | 6/2009 | Cross et al. |
| 7,565,969 B2 | 7/2009 | He |
| D606,854 S | 12/2009 | Greenhalgh |
| D610,983 S | 3/2010 | Wai |
| D611,806 S | 3/2010 | Bried |
| D613,903 S | 4/2010 | Wu et al. |
| D613,904 S | 4/2010 | Wu et al. |
| D616,753 S | 6/2010 | Beam et al. |
| 7,767,698 B2 | 8/2010 | Warchol et al. |
| 7,832,410 B2 | 11/2010 | Hon |
| D628,469 S | 12/2010 | Taylor et al. |
| D631,838 S | 2/2011 | Cheng |
| D636,257 S | 4/2011 | Bougoulas et al. |
| 7,992,554 B2 | 8/2011 | Radomski et al. |
| D649,658 S | 11/2011 | Belfance et al. |
| D650,738 S | 12/2011 | Leung |
| 8,113,343 B2 | 2/2012 | Åkerlind |
| D656,094 S | 3/2012 | Wu |
| 8,156,944 B2 | 4/2012 | Han |
| D661,016 S | 5/2012 | Borges et al. |
| D671,677 S | 11/2012 | Wu |
| D671,678 S | 11/2012 | Wu |
| 8,307,834 B1 | 11/2012 | Palmerino, Sr. et al. |
| D672,642 S | 12/2012 | Supranowicz |
| D674,539 S | 1/2013 | Wu |
| 8,365,742 B2 | 2/2013 | Hon |
| 8,375,957 B2 | 2/2013 | Hon |
| 8,393,331 B2 | 3/2013 | Hon |
| 8,430,106 B2 | 4/2013 | Potter et al. |
| 8,448,783 B2 | 5/2013 | Vecchi |
| 8,490,628 B2 | 7/2013 | Hon |
| 8,511,318 B2 | 8/2013 | Hon |
| D693,055 S | 11/2013 | Manca et al. |
| D700,397 S | 2/2014 | Manca et al. |
| 8,689,805 B2 | 4/2014 | Hon |
| 8,752,545 B2 | 6/2014 | Buchberger |
| 8,794,245 B1 | 8/2014 | Scatterday |
| 8,833,364 B2 | 9/2014 | Buchberger |
| D715,760 S | 10/2014 | Kim et al. |
| D716,267 S | 10/2014 | Kim et al. |
| 8,869,793 B1 | 10/2014 | Spandorfer et al. |
| 8,910,640 B2 | 12/2014 | Sears et al. |
| D720,884 S | 1/2015 | Liu |
| 8,948,578 B2 | 2/2015 | Buchberger |
| D723,738 S | 3/2015 | Liu |
| 8,967,155 B2 | 3/2015 | Bundren et al. |
| 9,055,617 B2 | 6/2015 | Thorens et al. |
| D736,460 S | 8/2015 | McKeon et al. |
| D737,507 S | 8/2015 | Liu |
| 9,609,894 B2 | 4/2017 | Abramov et al. |
| 9,623,205 B2 | 4/2017 | Buchberger |
| 9,730,276 B2 | 8/2017 | Vissa et al. |
| 9,943,108 B2 | 4/2018 | Lord |
| 9,961,939 B2 | 5/2018 | Reevell |
| 9,974,335 B2 | 5/2018 | Lord |
| 9,986,760 B2 | 6/2018 | Macko et al. |
| 10,010,695 B2 | 7/2018 | Buchberger |
| 10,045,562 B2 | 8/2018 | Buchberger |
| 10,278,421 B2 | 5/2019 | Lord |
| 10,368,582 B2 | 8/2019 | Lord |
| 2001/0004934 A1 | 6/2001 | Yamamoto et al. |
| 2001/0042546 A1 | 11/2001 | Umeda et al. |
| 2002/0005207 A1 | 1/2002 | Wrenn et al. |
| 2002/0016370 A1 | 2/2002 | Shytle et al. |
| 2002/0079309 A1 | 6/2002 | Cox et al. |
| 2003/0005620 A1 | 1/2003 | Ananth et al. |
| 2003/0049025 A1 | 3/2003 | Neumann et al. |
| 2003/0056791 A1 | 3/2003 | Nichols et al. |
| 2003/0064340 A1 | 4/2003 | Pappas |
| 2003/0079309 A1 | 5/2003 | Vandenbelt et al. |
| 2003/0106552 A1 | 6/2003 | Sprinkel, Jr. et al. |
| 2003/0108342 A1 | 6/2003 | Sherwood et al. |
| 2003/0108743 A1 | 6/2003 | Anderson |
| 2003/0168057 A1 | 9/2003 | Snyder et al. |
| 2003/0200964 A1 | 10/2003 | Blakley et al. |
| 2003/0202169 A1 | 10/2003 | Liu |
| 2004/0031485 A1 | 2/2004 | Rustad et al. |
| 2004/0056651 A1 | 3/2004 | Marietta Bersana |
| 2004/0129793 A1 | 7/2004 | Nguyen et al. |
| 2004/0210151 A1 | 10/2004 | Tsukashima et al. |
| 2004/0226568 A1 | 11/2004 | Takeuchi et al. |
| 2005/0063686 A1 | 3/2005 | Whittle et al. |
| 2005/0087460 A1 | 4/2005 | Bruhn et al. |
| 2005/0145260 A1 | 7/2005 | Inagaki et al. |
| 2005/0194013 A1 | 9/2005 | Wright |
| 2005/0204799 A1 | 9/2005 | Koch |
| 2005/0211243 A1 | 9/2005 | Esser |
| 2005/0224375 A1 | 10/2005 | Focke et al. |
| 2005/0235991 A1 | 10/2005 | Nichols et al. |
| 2005/0268911 A1 | 12/2005 | Cross et al. |
| 2006/0018840 A1 | 1/2006 | Lechuga-Ballesteros et al. |
| 2006/0078477 A1 | 4/2006 | Althouse et al. |
| 2006/0095311 A1 | 5/2006 | Thompson |
| 2006/0137681 A1 | 6/2006 | Von Hollen et al. |
| 2006/0180143 A1 | 8/2006 | Lind et al. |
| 2006/0196518 A1 | 9/2006 | Hon |
| 2006/0283468 A1 | 12/2006 | Lipowicz |
| 2007/0014549 A1 | 1/2007 | Demarest et al. |
| 2007/0045288 A1 | 3/2007 | Nelson |
| 2007/0062548 A1 | 3/2007 | Horstmann et al. |
| 2007/0102013 A1 | 5/2007 | Adams et al. |
| 2007/0107879 A1 | 5/2007 | Radomski et al. |
| 2007/0144514 A1 | 6/2007 | Yeates et al. |
| 2007/0155255 A1 | 7/2007 | Galauner et al. |
| 2007/0193895 A1 | 8/2007 | Weiss et al. |
| 2007/0267031 A1 | 11/2007 | Hon |
| 2007/0267032 A1 | 11/2007 | Shan |
| 2008/0017204 A1 | 1/2008 | Braunshteyn et al. |
| 2008/0092912 A1 | 4/2008 | Robinson et al. |
| 2008/0156326 A1 | 7/2008 | Belcastro et al. |
| 2008/0216828 A1 | 9/2008 | Wensley et al. |
| 2008/0223382 A1 | 9/2008 | Zeanah |
| 2008/0241255 A1 | 10/2008 | Rose et al. |
| 2009/0090472 A1 | 4/2009 | Radomski |
| 2009/0095311 A1 | 4/2009 | Han |
| 2009/0095312 A1 | 4/2009 | Herbrich et al. |
| 2009/0188490 A1 | 7/2009 | Han |
| 2009/0220222 A1 | 9/2009 | Rabin et al. |
| 2009/0241947 A1 | 10/2009 | Bedini et al. |
| 2009/0266837 A1 | 10/2009 | Gelardi et al. |
| 2009/0272379 A1 | 11/2009 | Thorens et al. |
| 2009/0288966 A1 | 11/2009 | Minarelli et al. |
| 2009/0293892 A1 | 12/2009 | Williams et al. |
| 2009/0324206 A1 | 12/2009 | Young et al. |
| 2010/0003904 A1 | 1/2010 | Duescher |
| 2010/0006113 A1 | 1/2010 | Urtsev et al. |
| 2010/0059070 A1 | 3/2010 | Potter et al. |
| 2010/0065653 A1 | 3/2010 | Wingo et al. |

(56) References Cited

U.S. PATENT DOCUMENTS

| | | |
|---|---|---|
| 2010/0083959 A1 | 4/2010 | Siller |
| 2010/0108059 A1 | 5/2010 | Axelsson et al. |
| 2010/0181387 A1 | 7/2010 | Zaffaroni et al. |
| 2010/0182608 A1 | 7/2010 | Zribi et al. |
| 2010/0211011 A1 | 8/2010 | Haar |
| 2010/0236546 A1* | 9/2010 | Yamada ............... A61M 11/042 128/200.21 |
| 2010/0242974 A1 | 9/2010 | Pan |
| 2010/0313901 A1 | 12/2010 | Fernando et al. |
| 2011/0011396 A1 | 1/2011 | Fang |
| 2011/0036363 A1 | 2/2011 | Urtsev et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0180433 A1 | 7/2011 | Rennecamp |
| 2011/0192914 A1 | 8/2011 | Ishigami |
| 2011/0209717 A1 | 9/2011 | Han |
| 2011/0226236 A1* | 9/2011 | Buchberger ......... A61M 11/042 128/200.23 |
| 2011/0277757 A1 | 11/2011 | Terry et al. |
| 2011/0278189 A1 | 11/2011 | Terry et al. |
| 2011/0290267 A1 | 12/2011 | Yamada et al. |
| 2011/0297166 A1 | 12/2011 | Takeuchi et al. |
| 2011/0303231 A1 | 12/2011 | Li et al. |
| 2011/0309157 A1 | 12/2011 | Yang et al. |
| 2012/0111347 A1 | 5/2012 | Hon |
| 2012/0145169 A1 | 6/2012 | Wu |
| 2012/0180994 A1 | 7/2012 | Yang et al. |
| 2012/0180995 A1 | 7/2012 | Yang et al. |
| 2012/0199146 A1 | 8/2012 | Marangos |
| 2012/0227752 A1 | 9/2012 | Alelov |
| 2012/0227753 A1 | 9/2012 | Newton |
| 2012/0242974 A1 | 9/2012 | LaValley et al. |
| 2012/0255567 A1 | 10/2012 | Rose et al. |
| 2012/0260927 A1 | 10/2012 | Liu |
| 2012/0285476 A1 | 11/2012 | Hon |
| 2013/0074857 A1 | 3/2013 | Buchberger |
| 2013/0081623 A1 | 4/2013 | Buchberger |
| 2013/0087160 A1 | 4/2013 | Gherghe |
| 2013/0098786 A1 | 4/2013 | Collins |
| 2013/0112214 A1 | 5/2013 | Bundren et al. |
| 2013/0142782 A1 | 6/2013 | Rahmel et al. |
| 2013/0192615 A1 | 8/2013 | Tucker et al. |
| 2013/0192619 A1 | 8/2013 | Tucker et al. |
| 2013/0192621 A1 | 8/2013 | Li et al. |
| 2013/0192623 A1 | 8/2013 | Tucker et al. |
| 2013/0213419 A1 | 8/2013 | Tucker et al. |
| 2013/0228191 A1* | 9/2013 | Newton ............... A61M 15/06 131/329 |
| 2013/0255702 A1 | 10/2013 | Griffith, Jr. et al. |
| 2013/0284192 A1 | 10/2013 | Peleg et al. |
| 2013/0306084 A1 | 11/2013 | Flick |
| 2013/0319407 A1 | 12/2013 | Liu |
| 2013/0333700 A1 | 12/2013 | Buchberger |
| 2013/0340779 A1 | 12/2013 | Liu |
| 2013/0341218 A1 | 12/2013 | Liu |
| 2013/0342157 A1 | 12/2013 | Liu |
| 2014/0000638 A1 | 1/2014 | Sebastian et al. |
| 2014/0007863 A1 | 1/2014 | Chen |
| 2014/0007892 A1 | 1/2014 | Liu |
| 2014/0020697 A1 | 1/2014 | Liu |
| 2014/0048086 A1 | 2/2014 | Zhanghua |
| 2014/0053831 A1 | 2/2014 | Leamon et al. |
| 2014/0060528 A1 | 3/2014 | Liu |
| 2014/0060554 A1 | 3/2014 | Collett et al. |
| 2014/0060555 A1 | 3/2014 | Chang et al. |
| 2014/0064715 A1 | 3/2014 | Greim et al. |
| 2014/0106155 A1 | 4/2014 | Iandoli Espinosa |
| 2014/0182608 A1 | 7/2014 | Egoyants et al. |
| 2014/0196717 A1 | 7/2014 | Liu |
| 2014/0196731 A1 | 7/2014 | Scatterday |
| 2014/0202454 A1 | 7/2014 | Buchberger |
| 2014/0202476 A1 | 7/2014 | Egoyants et al. |
| 2014/0209105 A1 | 7/2014 | Sears et al. |
| 2014/0216485 A1 | 8/2014 | Egoyants et al. |
| 2014/0238396 A1 | 8/2014 | Buchberger |
| 2014/0238423 A1 | 8/2014 | Tucker et al. |
| 2014/0238424 A1* | 8/2014 | Macko ................ A24F 40/44 131/328 |
| 2014/0261490 A1 | 9/2014 | Kane |
| 2014/0261495 A1 | 9/2014 | Novak, III et al. |
| 2014/0270726 A1 | 9/2014 | Egoyants et al. |
| 2014/0270730 A1 | 9/2014 | DePiano et al. |
| 2014/0283825 A1 | 9/2014 | Buchberger |
| 2014/0286630 A1 | 9/2014 | Buchberger |
| 2014/0299125 A1 | 10/2014 | Buchberger |
| 2014/0305431 A1 | 10/2014 | Holley et al. |
| 2014/0332019 A1 | 11/2014 | Liu |
| 2014/0338680 A1 | 11/2014 | Abramov et al. |
| 2015/0114411 A1 | 4/2015 | Buchberger |
| 2015/0128964 A1 | 5/2015 | Bundren et al. |
| 2015/0128971 A1* | 5/2015 | Verleur ............... H02J 7/0042 131/329 |
| 2015/0136756 A1 | 5/2015 | Vissa et al. |
| 2015/0157055 A1 | 6/2015 | Lord |
| 2015/0181934 A1 | 7/2015 | Lyubomirskiy et al. |
| 2015/0181937 A1 | 7/2015 | Dubief et al. |
| 2015/0196058 A1 | 7/2015 | Lord |
| 2015/0201675 A1 | 7/2015 | Lord |
| 2015/0208728 A1 | 7/2015 | Lord |
| 2016/0073693 A1 | 3/2016 | Reevell |
| 2016/0101909 A1 | 4/2016 | Schennum et al. |
| 2016/0106154 A1 | 4/2016 | Lord |
| 2016/0106155 A1 | 4/2016 | Reevell |
| 2016/0120218 A1 | 5/2016 | Schennum et al. |
| 2016/0278163 A1* | 9/2016 | Chen .................... A24F 40/485 |
| 2016/0353804 A1 | 12/2016 | Lord |
| 2017/0006916 A1 | 1/2017 | Liu |
| 2017/0007798 A1* | 1/2017 | Salmon ............ A61M 16/0666 |
| 2017/0027225 A1* | 2/2017 | Buchberger ............ A24F 40/46 |
| 2017/0042245 A1* | 2/2017 | Buchberger ............ A24F 40/50 |
| 2017/0188629 A1 | 7/2017 | Dickens et al. |
| 2017/0188630 A1 | 7/2017 | Buchberger |
| 2017/0197043 A1 | 7/2017 | Buchberger |
| 2017/0197044 A1 | 7/2017 | Buchberger |
| 2017/0197046 A1 | 7/2017 | Buchberger |
| 2018/0192705 A1 | 7/2018 | Lord |
| 2018/0235284 A1 | 8/2018 | Lord |
| 2019/0254350 A1 | 8/2019 | Lord |
| 2019/0289920 A1 | 9/2019 | Lord |

FOREIGN PATENT DOCUMENTS

| | | |
|---|---|---|
| AT | 507188 A4 | 3/2010 |
| AT | 508244 A4 | 12/2010 |
| AT | 510405 A4 | 4/2012 |
| AT | 510504 A1 | 4/2012 |
| AU | 6391373 A | 6/1975 |
| AU | 6393173 A | 6/1975 |
| AU | 2015359102 B2 | 6/2018 |
| BR | 6402132 U | 7/1986 |
| CA | 2309376 A1 | 11/2000 |
| CA | 2824970 A1 | 8/2012 |
| CH | 698603 B1 | 9/2009 |
| CL | 199400288 A1 | 8/1995 |
| CL | 199900377 | 3/1999 |
| CN | 2092880 U | 1/1992 |
| CN | 2220168 Y | 2/1996 |
| CN | 1126425 A | 7/1996 |
| CN | 1205849 A | 1/1999 |
| CN | 1312730 A | 9/2001 |
| CN | 1329567 A | 1/2002 |
| CN | 1333657 A | 1/2002 |
| CN | 2485265 Y | 4/2002 |
| CN | 2660914 Y | 12/2004 |
| CN | 1607911 A | 4/2005 |
| CN | 2719043 Y | 8/2005 |
| CN | 1694765 A | 11/2005 |
| CN | 1703279 A | 11/2005 |
| CN | 1286409 C | 11/2006 |
| CN | 2904674 Y | 5/2007 |
| CN | 200966824 Y | 10/2007 |
| CN | 101115901 A | 1/2008 |

(56) References Cited

FOREIGN PATENT DOCUMENTS

| | | |
|---|---|---|
| CN | 201023852 Y | 2/2008 |
| CN | 201238609 Y | 5/2009 |
| CN | 201240612 Y | 5/2009 |
| CN | 201375023 Y | 1/2010 |
| CN | 101648041 A | 2/2010 |
| CN | 201430913 Y | 3/2010 |
| CN | 101843368 A | 9/2010 |
| CN | 201592850 U | 9/2010 |
| CN | 101878958 A | 11/2010 |
| CN | 101925309 A | 12/2010 |
| CN | 201657770 U | 12/2010 |
| CN | 102014677 A | 4/2011 |
| CN | 201830900 U | 5/2011 |
| CN | 201860753 U | 6/2011 |
| CN | 102264249 A | 11/2011 |
| CN | 102264420 A | 11/2011 |
| CN | 102326869 A | 1/2012 |
| CN | 202122096 U | 1/2012 |
| CN | 102389166 A | 3/2012 |
| CN | 202172846 U | 3/2012 |
| CN | 102655773 A | 9/2012 |
| CN | 102753047 A | 10/2012 |
| CN | 202722498 U | 2/2013 |
| CN | 202750708 U | 2/2013 |
| CN | 103052380 A | 4/2013 |
| CN | 103338664 A | 10/2013 |
| CN | 103960782 A | 8/2014 |
| CN | 203986095 U | 12/2014 |
| CN | 204048047 U | 12/2014 |
| CN | 104602553 A | 5/2015 |
| CN | 204317492 U | 5/2015 |
| CN | 104684422 A | 6/2015 |
| CN | 104983079 A | 10/2015 |
| CN | 105310114 A | 2/2016 |
| CN | 105394816 A | 3/2016 |
| CN | 106102863 A | 11/2016 |
| CN | 106998820 B | 10/2019 |
| DE | 594585 | 3/1934 |
| DE | 1950439 A1 | 4/1971 |
| DE | 2653133 A1 | 5/1978 |
| DE | 2940797 A1 | 4/1981 |
| DE | 3148335 A1 | 7/1983 |
| DE | 3218760 A1 | 12/1983 |
| DE | 3936687 A1 | 5/1990 |
| DE | 29719509 U1 | 1/1998 |
| DE | 19630619 A1 | 2/1998 |
| DE | 19654945 A1 | 3/1998 |
| DE | 10330681 B3 | 6/2004 |
| DE | 202006013439 U1 | 10/2006 |
| DE | 202013100606 U1 | 2/2013 |
| EA | 019736 B1 | 5/2014 |
| EA | 022685 B1 | 2/2016 |
| EP | 0280262 A2 | 8/1988 |
| EP | 0295122 A2 | 12/1988 |
| EP | 0358002 A2 | 3/1990 |
| EP | 0358114 A2 | 3/1990 |
| EP | 0444553 A2 | 9/1991 |
| EP | 0488488 A1 | 6/1992 |
| EP | 0845220 A1 | 6/1998 |
| EP | 0847220 A2 | 6/1998 |
| EP | 0893071 A1 | 1/1999 |
| EP | 0893171 A1 | 1/1999 |
| EP | 1166814 A2 | 1/2002 |
| EP | 1166847 A2 | 1/2002 |
| EP | 1468618 A1 | 10/2004 |
| EP | 1736065 A1 | 12/2006 |
| EP | 1757921 A2 | 2/2007 |
| EP | 1820748 A1 | 8/2007 |
| EP | 1847671 A1 | 10/2007 |
| EP | 1950439 A1 | 7/2008 |
| EP | 2018886 A1 | 1/2009 |
| EP | 2022349 A1 | 2/2009 |
| EP | 2022350 A1 | 2/2009 |
| EP | 2113178 A1 | 11/2009 |
| EP | 2340729 A1 | 7/2011 |
| EP | 2358418 A1 | 8/2011 |
| EP | 2404515 A1 | 1/2012 |
| EP | 2468116 A1 | 6/2012 |
| EP | 2468118 A1 | 6/2012 |
| EP | 2698070 A1 | 2/2014 |
| EP | 2762019 A1 | 8/2014 |
| EP | 2785208 A1 | 10/2014 |
| EP | 2801273 A2 | 11/2014 |
| EP | 2835062 A1 | 2/2015 |
| EP | 2871985 A1 | 5/2015 |
| EP | 2907397 A1 | 8/2015 |
| EP | 2907397 B1 | 9/2017 |
| EP | 3117860 B1 | 1/2019 |
| EP | 3229621 B1 | 1/2020 |
| FR | 472030 A | 11/1914 |
| FR | 960469 A | 4/1950 |
| FR | 1292446 A | 5/1962 |
| GB | 190930472 | 12/1909 |
| GB | 191100628 A | 11/1911 |
| GB | 25575 A | 3/1912 |
| GB | 191311086 A | 9/1913 |
| GB | 110216 A | 10/1917 |
| GB | 111454 A | 11/1917 |
| GB | 120016 A | 10/1918 |
| GB | 160493 A | 3/1921 |
| GB | 163124 A | 5/1921 |
| GB | 215992 A | 5/1924 |
| GB | 220229 A | 8/1924 |
| GB | 268967 A | 4/1927 |
| GB | 402064 A | 11/1933 |
| GB | 507955 A | 6/1939 |
| GB | 544329 A | 4/1942 |
| GB | 565574 A | 11/1944 |
| GB | 611596 A | 11/1948 |
| GB | 626888 A | 7/1949 |
| GB | 871869 A | 7/1961 |
| GB | 1313525 A | 4/1973 |
| GB | 1046183 | 7/1988 |
| GB | 2275464 A | 8/1994 |
| GB | 2068034 | 11/1997 |
| GB | 2369108 A | 5/2002 |
| GB | 4000273 | 12/2006 |
| GB | 4006615 | 10/2008 |
| GB | 2504075 A | 1/2014 |
| GB | 2513635 A | 11/2014 |
| HK | 1196511 A1 | 10/2016 |
| HK | 1226611 | 10/2017 |
| JP | S5289386 A | 7/1977 |
| JP | S5752456 A | 3/1982 |
| JP | S57140354 A | 8/1982 |
| JP | S59106340 A | 6/1984 |
| JP | S6121542 B2 | 5/1986 |
| JP | S6196763 A | 5/1986 |
| JP | S6196765 A | 5/1986 |
| JP | H01117775 A | 5/1989 |
| JP | H02124081 A | 5/1990 |
| JP | H02124082 A | 5/1990 |
| JP | H0548944 A | 2/1993 |
| JP | H05103836 A | 4/1993 |
| JP | H05309136 A | 11/1993 |
| JP | 3003543 U | 10/1994 |
| JP | H06303837 A | 11/1994 |
| JP | H06315366 A | 11/1994 |
| JP | H07147965 A | 6/1995 |
| JP | H08299862 A | 11/1996 |
| JP | H08511176 A | 11/1996 |
| JP | H1189551 A | 4/1999 |
| JP | H11503912 A | 4/1999 |
| JP | H11514081 A | 11/1999 |
| JP | 3003543 B2 | 1/2000 |
| JP | 2001502542 A | 2/2001 |
| JP | 2001248842 A | 9/2001 |
| JP | 2002527153 A | 8/2002 |
| JP | 3093201 U | 4/2003 |
| JP | 2003226577 A | 8/2003 |
| JP | 2004332069 A | 11/2004 |
| JP | 2005013092 A | 1/2005 |
| JP | 2005138773 A | 6/2005 |
| JP | 2005524067 A | 8/2005 |

(56) References Cited

FOREIGN PATENT DOCUMENTS

| | | |
|---|---|---|
| JP | 2005537918 A | 12/2005 |
| JP | 2005537919 A | 12/2005 |
| JP | 2005538149 A | 12/2005 |
| JP | 2005538159 A | 12/2005 |
| JP | 2007057532 A | 3/2007 |
| JP | 2007512880 A | 5/2007 |
| JP | 2007297124 A | 11/2007 |
| JP | 2008544834 A | 12/2008 |
| JP | 2009509523 A | 3/2009 |
| JP | 2009526714 A | 7/2009 |
| JP | 2009529871 A | 8/2009 |
| JP | 2009537119 A | 10/2009 |
| JP | 2010080261 A | 4/2010 |
| JP | 2011087569 A | 5/2011 |
| JP | 2011515093 A | 5/2011 |
| JP | 2011518567 A | 6/2011 |
| JP | 2012013247 A | 1/2012 |
| JP | 2012026933 A | 2/2012 |
| JP | 2012029633 A | 2/2012 |
| JP | 2012057859 A | 3/2012 |
| JP | 2012506263 A | 3/2012 |
| JP | 2012249854 A | 12/2012 |
| JP | 2014501107 A | 1/2014 |
| JP | 2014511175 A | 5/2014 |
| JP | 2014524313 A | 9/2014 |
| JP | 2014525251 A | 9/2014 |
| JP | 2015505476 A | 2/2015 |
| JP | 2015513970 A | 5/2015 |
| JP | 2015521847 A | 8/2015 |
| JP | 6507248 B2 | 4/2019 |
| KR | 920017172 A | 9/1992 |
| KR | 100244670 B1 | 2/2000 |
| KR | 20050037919 A | 4/2005 |
| KR | 20100006995 U | 7/2010 |
| KR | 20110006928 U | 7/2011 |
| KR | 20120025569 A | 3/2012 |
| KR | 20120070731 A | 7/2012 |
| KR | 20130004985 A | 1/2013 |
| KR | 20130006714 A | 1/2013 |
| KR | 20130006714 U | 11/2013 |
| KR | 200470732 Y1 | 1/2014 |
| KR | 20140128449 A | 11/2014 |
| KR | 101955000 B1 | 3/2019 |
| KR | 102148901 B1 | 8/2020 |
| NL | 6617184 A | 6/1967 |
| PH | 12017500957 B1 | 10/2017 |
| RU | 2311859 C2 | 12/2007 |
| RU | 2328192 C1 | 7/2008 |
| RU | 2336001 C2 | 10/2008 |
| RU | 2360583 C1 | 7/2009 |
| RU | 89927 U1 | 12/2009 |
| RU | 94815 U1 | 6/2010 |
| RU | 103281 U1 | 4/2011 |
| RU | 115629 U1 | 5/2012 |
| RU | 121706 U1 | 11/2012 |
| RU | 122000 U1 | 11/2012 |
| RU | 124120 U1 | 1/2013 |
| RU | 132318 U1 | 9/2013 |
| RU | 2509516 C2 | 3/2014 |
| UA | 89752 C2 | 3/2010 |
| UA | 67598 U | 2/2012 |
| UA | 78167 U | 3/2013 |
| WO | WO-9527412 A1 | 10/1995 |
| WO | WO-9632854 A2 | 10/1996 |
| WO | WO-9748293 A1 | 12/1997 |
| WO | WO-9817131 A1 | 4/1998 |
| WO | WO-0009188 A1 | 2/2000 |
| WO | WO-0021598 A1 | 4/2000 |
| WO | WO-0028842 A1 | 5/2000 |
| WO | WO-0050111 A1 | 8/2000 |
| WO | WO-02051468 A2 | 7/2002 |
| WO | WO-02058747 A1 | 8/2002 |
| WO | WO-02060769 A1 | 8/2002 |
| WO | WO-03005045 A1 | 1/2003 |
| WO | WO-03028409 A1 | 4/2003 |
| WO | WO-03050405 A1 | 6/2003 |
| WO | WO-03083283 A1 | 10/2003 |
| WO | WO-03101454 A1 | 12/2003 |
| WO | WO-2004022128 A2 | 3/2004 |
| WO | WO-2004022242 A1 | 3/2004 |
| WO | WO-2004022243 A1 | 3/2004 |
| WO | WO-2005106350 A2 | 11/2005 |
| WO | WO-2006082571 A1 | 8/2006 |
| WO | WO-2007040941 A1 | 4/2007 |
| WO | WO-2007042941 A2 | 4/2007 |
| WO | WO-2007108877 A2 | 9/2007 |
| WO | WO-2007131448 A1 | 11/2007 |
| WO | WO-2007131449 A1 | 11/2007 |
| WO | WO-2007141668 A2 | 12/2007 |
| WO | WO-2008006048 A2 | 1/2008 |
| WO | WO-2008038144 A2 | 4/2008 |
| WO | WO-2008104870 A1 | 9/2008 |
| WO | WO-2009001085 A2 | 12/2008 |
| WO | WO-2009015410 A1 | 2/2009 |
| WO | WO-2009092862 A1 | 7/2009 |
| WO | WO-2009092419 A3 | 9/2009 |
| WO | WO-2009118085 A1 | 10/2009 |
| WO | WO-2009132793 A1 | 11/2009 |
| WO | WO-2010045670 A1 | 4/2010 |
| WO | WO-2010045671 A1 | 4/2010 |
| WO | WO-2011050943 A1 | 5/2011 |
| WO | WO-2011050964 A1 | 5/2011 |
| WO | WO-2011079932 A1 | 7/2011 |
| WO | WO-2011109849 A1 | 9/2011 |
| WO | WO-2011137453 A2 | 11/2011 |
| WO | WO-2012025496 A1 | 3/2012 |
| WO | WO-2012065310 A1 | 5/2012 |
| WO | WO-2012065754 A2 | 5/2012 |
| WO | WO-2012085203 A1 | 6/2012 |
| WO | WO-2012085207 A1 | 6/2012 |
| WO | WO-2012106739 A1 | 8/2012 |
| WO | WO-2012114082 A1 | 8/2012 |
| WO | WO-2013013808 A1 | 1/2013 |
| WO | WO-2013025921 A1 | 2/2013 |
| WO | WO-2013034453 A1 | 3/2013 |
| WO | WO-2013034460 A1 | 3/2013 |
| WO | WO-2013045942 A2 | 4/2013 |
| WO | WO-2013057185 A1 | 4/2013 |
| WO | WO-2013082173 A1 | 6/2013 |
| WO | WO-2013083631 A1 | 6/2013 |
| WO | WO-2013098395 A1 | 7/2013 |
| WO | WO-2013116558 A1 | 8/2013 |
| WO | WO-2013116571 A1 | 8/2013 |
| WO | WO-2013116572 A1 | 8/2013 |
| WO | WO-2013142671 A1 | 9/2013 |
| WO | WO-2013152873 A1 | 10/2013 |
| WO | WO-2013178769 A1 | 12/2013 |
| WO | WO-2013189050 A1 | 12/2013 |
| WO | WO-2013189052 A1 | 12/2013 |
| WO | WO-2014005275 A1 | 1/2014 |
| WO | WO-2014012906 A1 | 1/2014 |
| WO | WO-2014015463 A1 | 1/2014 |
| WO | WO-2014061477 A1 | 4/2014 |
| WO | WO-2014071329 A1 | 5/2014 |
| WO | 2014106329 A1 | 7/2014 |
| WO | 2014130772 A1 | 8/2014 |
| WO | WO-2014130695 A1 | 8/2014 |
| WO | WO-2014140320 A1 | 9/2014 |
| WO | WO-2014150131 A1 | 9/2014 |
| WO | WO-2015114327 A1 | 8/2015 |
| WO | WO-2015114328 A1 | 8/2015 |
| WO | WO-2015165812 A1 | 11/2015 |

OTHER PUBLICATIONS

Application and File History for U.S. Appl. No. 13/125,343, filed Apr. 21, 2011, inventor Buchberger.

Application and File History for U.S. Appl. No. 13/984,512, filed Aug. 29, 2013, inventor Buchberger.

Application and File History for U.S. Appl. No. 14/235,210, filed Mar. 4, 2014, inventor Buchberger, 504 pages.

Application and File History for U.S. Appl. No. 14/268,909, filed May 2, 2014, inventor Buchberger.

(56) References Cited

OTHER PUBLICATIONS

Application and File History for U.S. Appl. No. 14/296,803, filed Jun. 5, 2014, inventor Buchberger, 627 pages.
Application and File History for U.S. Appl. No. 14/306,831, filed Jun. 17, 2014, inventor Buchberger.
Application and File History for U.S. Appl. No. 14/353,256, filed Apr. 21, 2014, inventor Buchberger, 375 pages.
Application and File History for U.S. Appl. No. 14/594,065, filed Jan. 9, 2015, Inventor Buchberger, 302 pages.
Application and File History for U.S. Appl. No. 14/787,946, filed Oct. 29, 2015, inventor Lord, 228 pages.
Application and File History for U.S. Appl. No. 14/888,514, filed Nov. 2, 2015, inventor Reevell, 188 pages.
Application and File History for U.S. Appl. No. 14/888,517, filed Nov. 2, 2015, Inventor Reevell, 136 pages.
Application and File History for U.S. Appl. No. 15/307,095, filed Oct. 27, 2016, inventor Buchberger, 288 pages.
Application and File History for U.S. Appl. No. 15/454,156, filed Mar. 9, 2017, inventor Buchberger, 61 pages.
Application and File History for U.S. Appl. No. 15/470,078, filed Mar. 27, 2017, inventor Buchberger, 392 pages.
Application and File History for U.S. Appl. No. 15/470,089, filed Mar. 27, 2017, inventor Buchberger, 558 pages.
Application and File History for U.S. Appl. No. 15/470,095, filed Mar. 27, 2017, inventor Buchberger, 351 pages.
Application and File History for U.S. Appl. No. 15/997,113, filed Jun. 4, 2018, inventor Buchberger.
Application and File History for U.S. Appl. No. 16/096,554, filed Oct. 25, 2018, Inventor Fraser.
Company Filtrona Richmond Inc., http://www.filtronaporoustechnologies.com, Nov. 19, 2018, 1 page.
Decision on Appeal, U.S. Appl. No. 14/306,831, mailing date Mar. 26, 2020, 6 pages.
Decision to Grant a Patent mailed May 22, 2018 for Japanese Application No. 2016-134648, 5 pages.
Decision to Grant dated Feb. 5, 2018 for Ukraine Application No. 201607243, 6 pages.
Decision to Grant dated Apr. 11, 2016 for Russian Application No. 2015100321, 8 pages (No translation available).
Decision to Grant dated Jun. 23, 2016 for Ukrainian Application No. 201500198, 6 pages (No translation available).
Decision to Grant dated Apr. 27, 2017 for Russian Application No. 2015146845, 8 pages.
Decision to Grant for Australian Application No. 2017105898, dated Mar. 16, 2018, 12 pages.
Decision to Grant for Great Britain Application No. GB1405720.2, mailed Sep. 26, 2017, 2 pages.
Decision to Grant for Russian Application No. 120267, dated Oct. 26, 2016, 7 pages.
Decision to Grant mailed Apr. 1, 2014 for Russian Application No. 2011120430, 16 pages.
Decision to Grant mailed Aug. 5, 2014 for Japanese Application No. 2011-532464, 6 pages.
Diener Electronic, "Plasma Polymerization," The company Diener electronic GmbH+Co. KG, Retrieved on Oct. 17, 2017, 19 pages.
Dunn P.D., et al., "Heat Pipes," Fourth Edition, Pergamon, ISBN0080419038, 1994, 14 pages.
ECF, "Welcome to the World's Largest E-Cigarette Website: The Voice of Vaping since 2007," Oct. 2011, Nichrome or Kanthal Specs for Purchasing, retrieved on Apr. 19, 2020, 6 pages.
Examination Report for Great Britain Application No. GB1405720. 2, dated Jun. 27, 2017, 3 pages.
Examination Report mailed Nov. 20 for Australian Application No. 2017256084, 3 pages.
Examination Report mailed Dec. 15, 2017, for Australian Application No. 201512626, 3 pages.
Extended European Search Report for Application No. 15178588, mailed on Apr. 14, 2016, 2 pages.
Extended European Search Report for Application No. 16166656, mailed on Oct. 11, 2016, 9 pages.
Extended European Search Report for Application No. 17189951.1, mailed on Jan. 4, 2018, 11 pages.
Extended European Search Report for Application No. 18205608.5, mailed on Jul. 12, 2019, 7 pages.
Extended European Search Report for Application No. EP17197150. 5, mailed on Mar. 1, 2018, 6 pages.
Extended European Search Report for Application No. 16151458.3, mailed Jul. 11, 2016, 8 pages.
Extended European Search Report for Application No. 19196432.9, mailed on Dec. 9, 2019, 14 pages.
Extended European Search Report for European Application No. 15178588, mailed on Apr. 22, 2016, 4 pages.
First Office Action for Chinese Application No. 201480031926.5 dated Apr. 21, 2017, 12 pages.
First Office Action mailed Dec. 3, 2012 for Chinese Application No. 200980152395.4, 16 pages.
Hegbom T., "Integrating Electrical Heating Elements in Appliance Design," resulting in interlocutory decision dated Aug. 7, 2019, 4 pages.
Hong Kong Publication, Application No. 14110165.2, published on Dec. 19, 2014, 1 page.
Hong Kong Publication, Application No. 16113324.2, published on Oct. 6, 2017, 1 page.
Iatty, "An Idea of the Iatty, Welcome to the World's Largest E-Cigarette Website: The Voice of Vaping since 2007," retrieved on Dec. 17, 2019, p. 23, Post 443 and 445, 7 pages.
Iatty, "An Idea of the Iatty, Welcome to the World's Largest E-Cigarette Website: The Voice of Vaping since 2007," retrieved on Dec. 17, 2019, p. 24, Post 467, 6 pages.
Iatty, "An Idea of the Iatty, Welcome to the World's Largest E-Cigarette Website: The Voice of Vaping since 2007," retrieved on Dec. 17, 2019, p. 37, Post 727, 6 pages.
Iatty, "An Idea of the Iatty, Welcome to the World's Largest E-Cigarette Website: The Voice of Vaping since 2007," retrieved on Dec. 17, 2019, Page, Post 1, 7 pages.
"Integrating Electrical Heating Elements in Product Design," Metallic Resistance Heating Wire, Chapter 1, Section 1.1 to 1.3.2, resulting in interlocutory decision dated Aug. 7, 2019, 6 pages.
"Integrating Electrical Heating Elements in Product Design," Metallic Resistance Heating Wire, Chapter 1, Section 1.4, resulting in interlocutory decision dated Aug. 7, 2019, 1 page.
"Integrating Electrical Heating Elements in Product Design," Metallic Resistance Heating Wire, resulting in interlocutory decision dated Aug. 7, 2019, 8 pages.
International Preliminary Report on Patentability for Application No. PCT/AT2009/000413, mailed on May 5, 2011, 7 pages.
International Preliminary Report on Patentability for Application No. PCT/AT2009/000414, mailed on Apr. 26, 2011, 7 pages.
International Preliminary Report on Patentability for Application No. PCT/AT2012/000017, mailed on Aug. 13, 2013, 5 pages.
International Preliminary Report on Patentability for Application No. PCT/EP2012/003103, mailed on Feb. 6, 2014, 7 pages.
International Preliminary Report on Patentability for Application No. PCT/EP2012/070647, dated on Apr. 22, 2014, 8 pages.
International Preliminary Report on Patentability for Application No. PCT/GB2014/051332, mailed on Nov. 12, 2015, 7 pages.
International Preliminary Report on Patentability for Application No. PCT/GB2014/051333, mailed on Aug. 5, 2015, 12 pages.
International Preliminary Report on Patentability for Application No. PCT/GB2014/051334, mailed on Nov. 12, 2015, 7 pages.
International Preliminary Report on Patentability for Application No. PCT/GB2014/051688, mailed on Dec. 17, 2015, 6 pages.
International Preliminary Report on Patentability for Application No. PCT/GB2015/050195, mailed May 13, 2016, 17 pages.
International Preliminary Report on Patentability for Application No. PCT/GB2015/051213, mailed on Jul. 14, 2016, 20 pages.
International Preliminary Report on Patentability for Application No. PCT/GB2015/053445, mailed on Jan. 24, 2017, 19 pages.
International Preliminary Report on Patentability for Application No. PCT/GB2017/051139, mailed on Aug. 6, 2018, 7 pages.
International Preliminary Report on Patentability mailed Sep. 9, 2014 for Application No. PCT/EP2013/64922, filed Jul. 15, 2013, 10 pages.

(56) References Cited

OTHER PUBLICATIONS

International Search Report and Written Opinion for Application No. PCT/AT2012/000017, mailed on Jul. 3, 2012, 6 pages.
International Search Report and Written Opinion for Application No. PCT/EP2012/003103, mailed on Nov. 26, 2012, 6 pages.
International Search Report and Written Opinion for Application No. PCT/EP2012/070647, mailed on Feb. 6, 2013, 9 pages.
International Search Report and Written Opinion for Application No. PCT/GB2014/051332, mailed on Jul. 21, 2014, 8 pages.
International Search Report and Written Opinion for Application No. PCT/GB2014/051333, mailed on Jul. 17, 2014, 10 pages.
International Search Report and Written Opinion for Application No. PCT/GB2014/051334, mailed on Jul. 21, 2014, 8 pages.
International Search Report and Written Opinion for Application No. PCT/GB2015/053445, mailed on Apr. 18, 2016, 21 pages.
International Search Report and Written Opinion for Application No. PCT/GB2017/051139, mailed on Aug. 9, 2017, 14 pages.
International Search Report and Written Opinion mailed Oct. 11, 2013 for Application No. PCT/EP2013/064922, filed Jul. 15, 2013, 6 pages.
International Search Report for App No. PCT/GB2015/050195, mailed Sep. 2, 2015, 4 pages.
International Search Report for Application No. PCT/AT2009/000413, mailed on Jan. 25, 2010, 3 pages.
International Search Report for Application No. PCT/AT2009/000414, mailed on Jan. 26, 2010, 2 pages.
International Search Report for Application No. PCT/GB2014/051633, mailed on Dec. 4, 2014, 7 pages.
International Search Report for Application No. PCT/GB2014/051688, mailed on Aug. 26, 2014, 4 pages.
International Search Report for Application No. PCT/GB2015/051213, mailed on Jul. 16, 2015, 5 pages.
Kynol, "Standard Specifications of Kynol™ Activated Carbon Fiber Products," Sep. 19, 2013, 2 pages.
Iatty, "E-Cigarette Forum," p. 10, May 2011, commentary by Imeothanasis and Iorderos33, retrieved on Feb. 11, 2019, 8 pages.
Notice of Allowance mailed Oct. 18, 2019 for Korean Application No. 1020167018457, 2 pages (with translation—3 pages).
Notice of Allowance mailed May 30, 2017 for Korean Application No. 1020157001277, 4 pages (No translation available).
Notice of Allowance mailed Jun. 27, 2018 for Korean Application No. 1020167020977, 3 pages.
Notice of Opposition Letter from EPO Opposition against the European Application No. 2358418, mailed Mar. 1, 2017, 60 pages.
Notice of Opposition mailed Oct. 30, 2019 for European Application No. 16166656.5, 39 pages.
Notice of Reasons for Rejection mailed Oct. 15, 2013 for Japanese Application No. 2011532464, 6 pages.
Notice of Reasons for Rejection mailed May 23, 2017 for Japanese Application No. 2016134648, 18 pages.
Notice of Reasons for Rejection mailed May 31, 2016 for Japanese Application No. 2015-137361, 6 pages.
Notice of Reasons for Rejection mailed Oct. 7, 2013 for Japanese Application No. 2011532464, 6 pages.
Notice of Reasons for Rejection mailed Sep. 8, 2015 for Japanese Application No. 2014179732, 5 pages.
Notice of Reasons for Revocation mailed Apr. 17, 2017 for Japanese Patent No. 5960358, with English translation, 12 pages.
Notification of Transmittal of IPRP for International Application No. PCT/GB2014/051633 dated Oct. 23, 2015, 9 pages.
Notification to Grant Patent Right for Invention mailed Oct. 25, 2018 for Chinese Application No. 201610086101.4, 2 pages.
Office Action and Search Report mailed Feb. 28, 2019 for Japanese Application No. 2018-088088, 25 pages.
Office Action dated Sep. 3, 2014, for Russian Application No. 2013504605, 7 pages.
Office Action dated Jul. 2, 2020 for Chinese Application No. 201780020023.0 filed Sep. 25, 2018, 22 pages.
Office Action dated Nov. 21, 2017 for Russian Application No. 2016142584, 8 pages.
Office Action dated Nov. 22, 2016 for Canadian Application No. 2878951, 3 pages.
Office Action dated Sep. 22, 2017 for Russian Application No. 2015146847, 11 pages.
Office Action dated Nov. 23, 2018 for Korean Application No. 1020167018457, 6 pages (12 pages with translation).
Office Action dated Apr. 25, 2017 for Japanese Application No. 2016123816, 2 pages (No translation available).
Office Action dated May 12, 2017 for Korean Application No. 10-20157034538, 10 pages.
Office Action for European Application No. 16166656, mailed on Jul. 29, 2020, 7 pages.
Office Action for Chilean Application No. 201701486 mailed Nov. 11, 2019, 10 pages.
Office Action for Chinese Application No. 201480031296.1 dated Mar. 27, 2017, 13 pages.
Office Action mailed Jun. 2, 2016 for Chinese Application No. 201380038075.2, 7 pages (with translation—19 pages).
Office Action mailed Sep. 11, 2017 for Chinese Application No. 201480024988.3, 10 pages.
Office Action mailed Dec. 12, 2018 for Korean Application No. 10-2017-7015164, 3 pages.
Office Action mailed Jun. 15, 2018 for Korean Application No. 10-2017-7015164, 13 pages.
Office Action mailed Mar. 16, 2020 for Chinese Patent Application No. 201610255788.X, filed Oct. 21, 2009, 21 pages.
Office Action mailed Jan. 18, 2017 for Chinese Application No. 201480024978.X, 8 pages.
Office Action mailed Jul. 18, 2018 for Chinese Application No. 201580022356.8, 15 pages.
Office Action mailed Sep. 22, 2017 for Russian Application No. 2014120213, 11 pages.
Office Action mailed Jan. 25, 2019 for European Application No. 17189951.1, 4 pages.
Office Action mailed Jun. 26, 2018 for Japanese Application No. 2017-530762, 16 pages.
Office Action mailed Nov. 26, 2019 for Brazilian Application No. 112015000872, 4 pages.
Office Action mailed Oct. 26, 2016 for Russian Application No. 2014120213, 7 pages.
Office Action mailed Sep. 27, 2019 for Korean Application No. 10-20197005785, 13 pages.
Office Action mailed Dec. 30, 2016 for Chinese Application No. 201480024988.3, 26 pages.
Office Action mailed Sep. 30, 2018 for Chinese Application No. 201610371843.1, 8 pages.
Office Action mailed May 4, 2018 for Chinese Application No. 201610086101.4, 7 pages.
Office Action mailed Dec. 5, 2017 for Japanese Application No. 2016-564977, 6 pages.
Office Action mailed Apr. 10, 2019, for Korean Application No. 1020167018457, 13 pages.
Office Action mailed Apr. 23, 2018 for Chinese Application No. 201580006377.0, 9 pages (20 pages with translation).
Office Action mailed Dec. 8, 2017 for Korean Application No. 1020167020977, 13 pages.
Office Action mailed Jan. 23, 2018, for Japanese Application No. 2016548373,3 pages, (6 pages with translation).
Office Action mailed Jun. 5, 2018, for Chinese Application No. 201610552323.0, 11 pages, (18 pages with translation).
Office Action mailed Mar. 14, 2018, for Russian Application No. 2016131333, 7 pages (13 pages with translation).
Opposition Statement dated Mar. 30, 2017 for Japanese Patent No. 5960358, 144 pages (No translation available).
Partial EPO Opposition, resulting in interlocutory decision dated Aug. 7, 2019, 75 pages.
Rudolph G., "The Influence of $CO_2$ on the Sensory Characteristics of the Favor-System," 1987, Accessed at http://legacy.library.ucsf.edu/tid/sld5f100, 24 pages.
Search Report for Chilean Application No. 2019-11665, mailed Nov. 11, 2019, 10 pages.
Search Report for Japanese Application No. 2011532464, mailed Sep. 18, 2013, 116 pages.

(56) References Cited

OTHER PUBLICATIONS

Search Report for Japanese Application No. 2014-179732, mailed Sep. 9, 2015, 12 pages.
Search Report for Japanese Application No. 2016134648, mailed Mar. 28, 2017, 29 pages.
Search Report for Japanese Application No. 2016-564977, mailed Oct. 25, 2017, 19 pages.
Search Report for Japanese Application No. 2011532464, mailed Sep. 24, 2013, 53 pages.
Search Report mailed Feb. 1, 2017 for Japanese Application No. 2016517671, 13 pages.
Search Report mailed Apr. 14, 2017 for Japanese Application No. 2016-134648, 31 pages.
Search Report mailed Sep. 19, 2013 for Japanese Application No. 2011-532464, 116 pages.
Search Report mailed Apr. 24, 2017 for Russian Application No. 2015146843, 3 pages.
Search Report mailed Jun. 24, 2019 for Russian Application No. 2018137583, 2 pages.
Search Report mailed Apr. 25, 2018 for Chinese Application No. 201610086101.4, 1 page.
Search Report mailed Aug. 25, 2015 for Japanese Application No. 2014-179732, 10 pages.
Search Report mailed Oct. 25, 2017 for Japanese Application No. 2016-864977, 19 pages.
Search Report mailed Apr. 29, 2019 for Russian Application No. 2018137501, 12 pages.
Search Report mailed May 29, 2015 for Great Britain Application No. 1422018, 3 pages.
Search Report mailed Mar. 20, 2015, for Great Britain Application No. GB1401520.0, 2 pages.
Second Office Action mailed Aug. 20, 2013 for Chinese Application No. 200980152395.4, 16 pages.
Sharafat et al., "Ceramic Foams: Inspiring New Solid Breeder Materials," 12th International Workshop on Ceramic Breeder Blanket Interactions, Germany, Sep. 16-17, 2004, 22 pages.
Supulveda et al., "Processing of Cellular Ceramics by Foaming and In Situ Polymerisation of Organic Monomers," Loughborough University, 1999, 22 pages.
Wires.co.uk, "Bare Nickel Chrome/Nichrome Section," Jun. 20, 2012, 33 pages.
Wires.co.uk, "Specialist in Craft Wire," Jun. 20, 2012, 5 pages.
Written Opinion for Application No. PCT/AT2009/000413, mailed on Jan. 25, 2010, 5 pages.
Written Opinion for Application No. PCT/AT2009/000414, mailed on Jan. 26, 2010, 14 pages.
Written Opinion for Application No. PCT/AT2012/000017, mailed on Jul. 3, 2012, 4 pages.
Written Opinion for Application No. PCT/GB2014/051633, mailed on Dec. 4, 2014, 11 pages.
Written Opinion for Application No. PCT/GB2014/051688, mailed on Aug. 26, 2014, 4 pages.
Written Opinion for Application No. PCT/GB2015/051213, mailed on Jul. 16, 2015, 9 pages.
Written Opinion mailed Jun. 23, 2014 for Application No. PCT/EP2013/064922, filed Jul. 15, 2013, 4 pages.
Written Opinion of the International Preliminary Examining Authority for Application No. PCT/GB2015/050195 mailed Jan. 20, 2016, 8 pages.
Written Opinion of the International Searching Authority for Application No. PCT/GB2015/050195, mailed Sep. 2, 2015, 8 pages.

* cited by examiner

AEROSOL PROVISION SYSTEMS

CROSS-REFERENCE TO RELATED APPLICATIONS

The present application is a Continuation of U.S. application Ser. No. 15/533,296 filed Jun. 5, 2017, which is a National Phase entry of PCT Application No. PCT/GB2015/053445, filed Nov. 13, 2015, which claims priority from GB Patent Application No. 1422018.0, filed Dec. 11, 2014, each of which is hereby fully incorporated herein by reference.

FIELD

The present disclosure relates to aerosol provision systems such as, but not exclusively, nicotine delivery systems (e.g. e-cigarettes).

BACKGROUND

Aerosol provision systems such as e-cigarettes generally contain a reservoir of a source liquid containing a formulation, typically including nicotine, from which an aerosol is generated, e.g. through vaporization or other means. Thus an aerosol source for an aerosol provision system may comprise a heating element coupled to a portion of the source liquid from the reservoir. When a user inhales on the device, the heating element is activated to vaporize a small amount of the source liquid, which is thus converted to an aerosol for inhalation by the user. More particularly, such devices are usually provided with one or more air inlet holes located away from a mouthpiece of the system. When a user sucks on the mouthpiece, air is drawn in through the inlet holes and past the aerosol source. There is a flow path connecting between the aerosol source and an opening in the mouthpiece so that air drawn past the aerosol source continues along the flow path to the mouthpiece opening, carrying some of the aerosol from the aerosol source with it. The aerosol-carrying air exits the aerosol provision system through the mouthpiece opening for inhalation by the user.

One important consideration for aerosol provision systems is the manner in which liquid is supplied to the heating element. On the one hand there is a need to supply source liquid to replace that vaporized during use to provide continued aerosol generation and to help avoid overheating caused by the heating element becoming dry. However, on the other hand, there is a need to restrict the supply source liquid to the heating element to avoid leakage from the aerosol provision system, for example due to excess liquid from the heating element running through the airflow channel to an aerosol outlet (mouthpiece) for the aerosol provision system. It can also be important to provide for an appropriate supply of liquid to the heating element for a range of different orientations in which a device might be held. Another important consideration for aerosol provision systems is the need to support what can be relatively fragile heating elements in an appropriate manner.

In this regard, various approaches for mounting heating elements in relation to a supply of source liquid in aerosol provision systems have been previously proposed. For example, US 2013/0333700 and WO 2013/057185 describe approaches in which a composite wick is fed by a remotely mounted reservoir, KR 20130004985 discloses a wick and heating element arranged in a conduit which is mounted transversely in an air channel with the wick extending into a surrounding reservoir and WO 2013/083631 describes a device in which a heating element is mounted adjacent a porous reservoir wall. However, the inventors have recognized the previously-proposed approaches do not always provide for an appropriate supply of source liquid and can be relatively complicated to manufacture.

Accordingly there remains a need for approaches which seek to ameliorate some of the drawbacks associated with existing schemes for mounting and supplying source liquid to heating elements in aerosol provision systems.

SUMMARY

According to a first aspect of certain embodiments, there is provided an apparatus for an electronic aerosol provision system comprising: a reservoir for a source liquid; and a carrier module that defines an airflow path within the reservoir and comprises a heating element supported in the airflow path within the reservoir for generating an aerosol from the source liquid, wherein the carrier module comprises a first part and a second part which cooperatively engage to support the heating element, wherein the first part and the second part of the carrier module cooperatively engage at an interface which extends in a direction that is substantially parallel to a direction along which air flows in the airflow path when the apparatus is in normal use.

According to a second aspect of certain embodiments, there is provided an electronic aerosol provision system comprising an apparatus according to the above-mentioned first aspect and a power source configured to supply electrical power to the heating element to generate an aerosol from the source liquid.

These and further aspects of certain embodiments are set out in the appended independent and dependent claims. It will be appreciated that features of the dependent claims may be combined with each other and features of the independent claims in combinations other than those explicitly set out in the claims. Furthermore, the approach described herein is not restricted to specific embodiments such as set out below, but includes and contemplates any appropriate combinations of features presented herein. For example, an electronic aerosol provision system may be provided in accordance with the approach described herein which includes any one or more of the various features described below as appropriate.

BRIEF DESCRIPTION OF THE DRAWINGS

Various embodiments will now be described in detail by way of example only with reference to the following drawings.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to an aerosol provision system, such as an e-cigarette. Throughout the following description the term "e-cigarette" may sometimes be used; however, it will be appreciated this term may be used interchangeably with aerosol (vapor) provision system.

Figure 1:
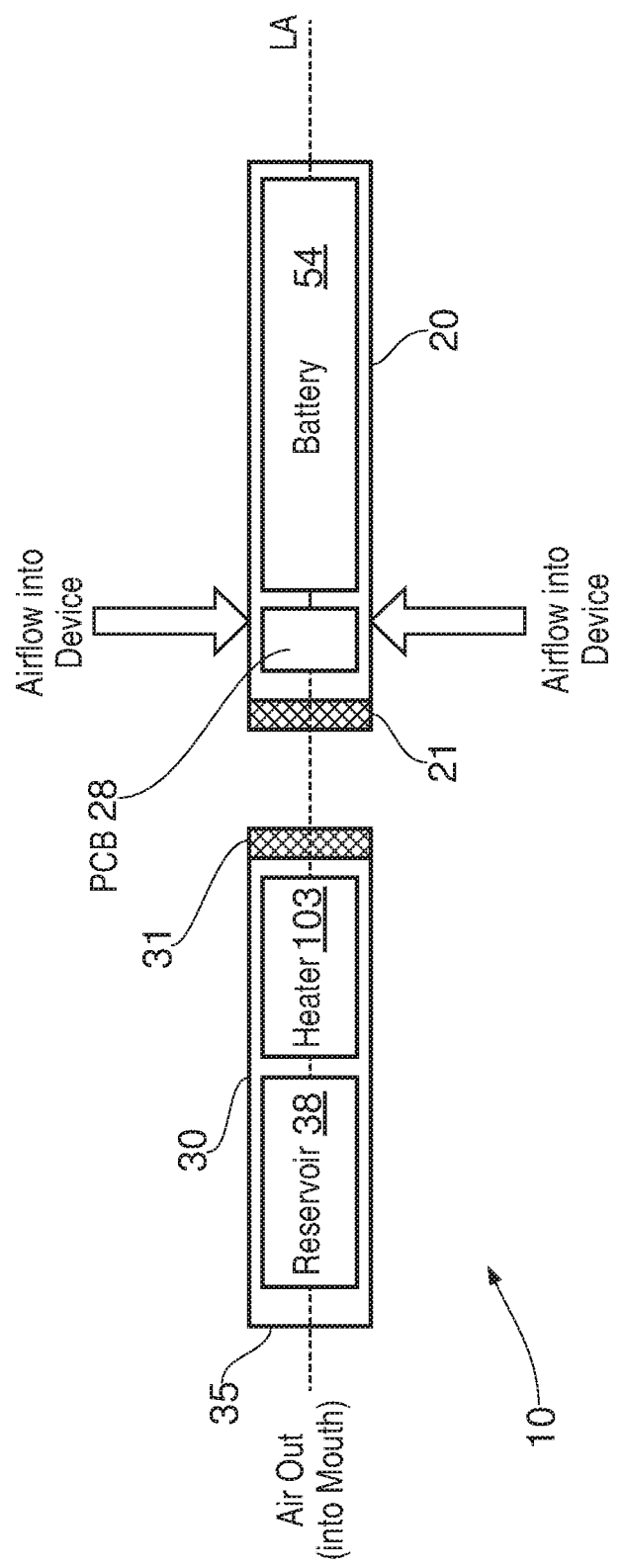
FIG. 1 is a schematic diagram of an aerosol provision system such as an e-cigarette in accordance with some embodiments.

FIG. 1 is a highly schematic diagram of an aerosol/vapor provision system such as an e-cigarette 10 in accordance with some embodiments (not to scale). The e-cigarette 10 has a generally cylindrical shape, extending along a longitudinal axis indicated by dashed line LA, and comprises two main components, namely a body 20 and a cartridge assembly (cartomizer) 30.

The cartridge assembly 30 includes a reservoir (chamber) 38 containing a source liquid comprising a liquid formulation from which an aerosol is to be generated, for example containing nicotine, and a heating element (distiller) 103 for heating source liquid to generate the aerosol. The source liquid and the heating element 103 may be collectively referred to as an aerosol source. The cartridge assembly 30 further includes a mouthpiece 35 having an opening through which a user may inhale the aerosol generated by the heating element 103. The source liquid may be of a conventional kind used in e-cigarettes, for example comprising around 1 to 3% nicotine and 50% glycerol, with the remainder comprising roughly equal measures of water and propylene glycol, and possibly also comprising other components, such as flavorings. The body 20 includes a re-chargeable cell or battery to provide power for the e-cigarette 10 and a circuit board for generally controlling the e-cigarette 10. In use, when the heating element 103 receives power from the battery, as controlled by the circuit board, the heating element 103 vaporizes source liquid at the heating location to generate the aerosol, and this is then inhaled by a user through the opening in the mouthpiece 35. The aerosol is carried from the aerosol source to the mouthpiece 35 along an air channel that connects the aerosol source to the mouthpiece opening as a user inhales on the mouthpiece 35.

The main body 20 of the e-cigarette 10 includes a re-chargeable cell or battery 54 to provide power for the e-cigarette 10 (referred to hereinafter as a battery) and a printed circuit board (PCB) 28 and/or other electronics for generally controlling the e-cigarette 10.

In this particular example, the body 20 and cartridge assembly 30 are detachable from one another by separating in a direction parallel to the longitudinal axis LA, as shown in FIG. 1, but are joined together when the device 10 is in use by cooperating engagement elements 21, 31 (e.g. forming a screw or bayonet fitting) to provide mechanical and electrical connectivity between the body 20 and the cartridge assembly 30. An electrical connector interface on the body 20 used to connect to the cartridge assembly 30 may also serve as an interface for connecting the body 20 to a charging device (not shown) when the body 20 is detached from the cartridge assembly 30. The other end of the charging device can be plugged into an external power supply, for example a USB socket, to charge or to re-charge the cell/battery in the body of the e-cigarette 10. In other implementations, a separate charging interface may be provided, for example so the battery 54 can be readily charged when still connected to the cartridge assembly 30.

The e-cigarette 10 is provided with one or more holes (not shown in FIG. 1) for air inlet. These holes connect to an airflow path through the e-cigarette 10 to the mouthpiece 35. The air flow path includes a region around the heating element 103 so that when a user inhales through the mouthpiece 35, air is drawn into the airflow path through the one or more air inlet holes, which are suitably located on the outside of the e-cigarette 10. This airflow (or the resulting change in pressure) is detected by a pressure sensor that in turn activates the heating element 103 to vaporize a portion of the source liquid to generate the aerosol. The airflow passes through the airflow path, and combines with the vapor in the region around the heating element 103 and the resulting aerosol (combination of airflow and condensed vapor) travels along the airflow path connecting from the region of the heating element 103 to the mouthpiece 35 to be inhaled by a user. The cartridge assembly 30 may be detached from the body 20 and disposed of when the supply of source liquid is exhausted (and replaced with another cartridge assembly if so desired). Alternatively, the cartridge 30 may be refillable.

Some embodiments described herein focus primarily on aspects of supplying source liquid to a suitably mounted heating element in an aerosol provision system, for example in a replaceable cartridge assembly of an e-cigarette. In this regard a main body component of aerosol provision systems in accordance with certain embodiments of the invention may be provided in accordance with generally conventional techniques.

Figure 2:
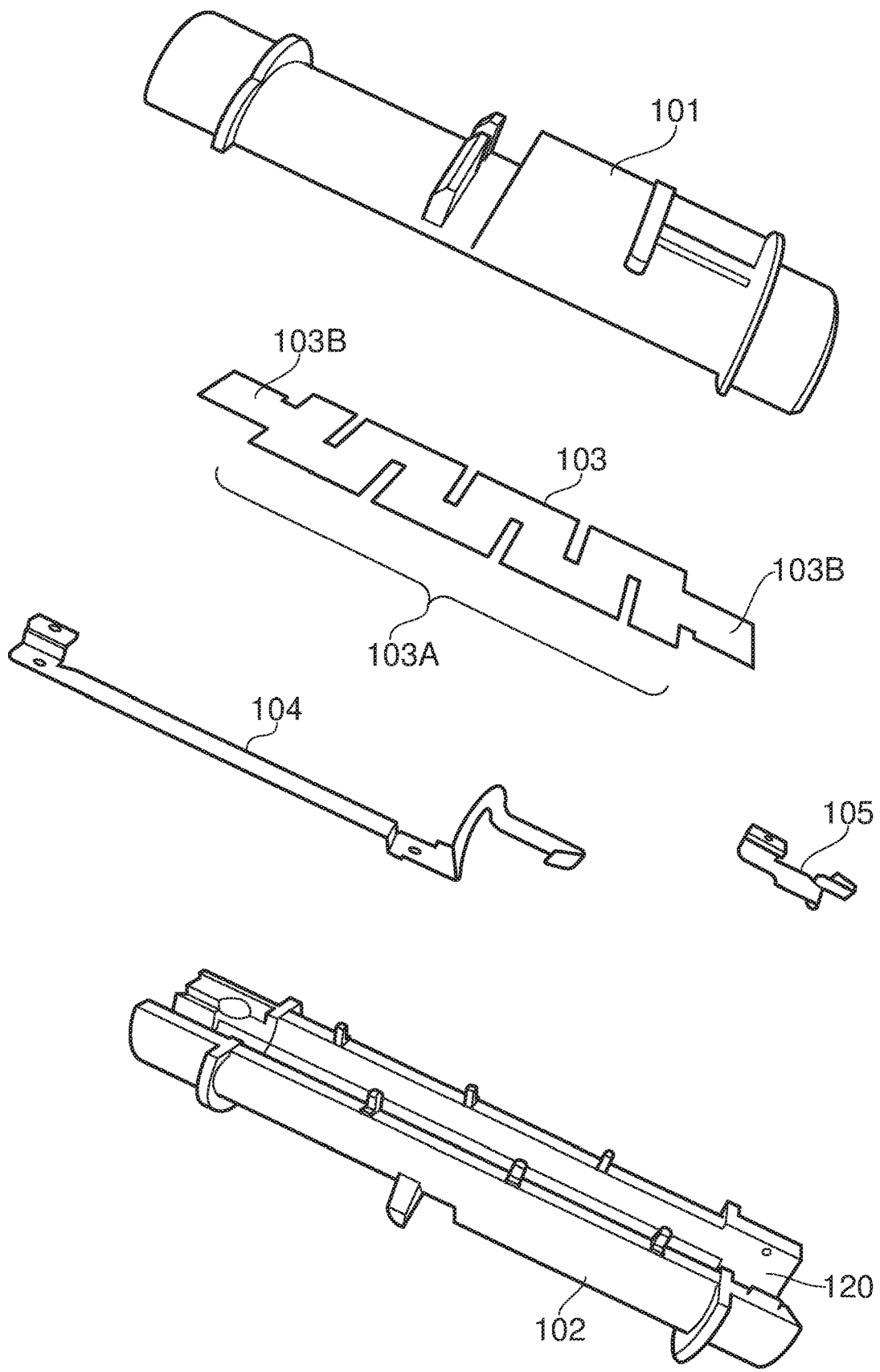
FIG. 2 schematically represents components of a heating element carrier module for use in a cartridge assembly of the aerosol provision system of FIG. 1 in accordance with some embodiments.

FIG. 2 schematically represents components of a heating element carrier module 160 for use in a cartridge assembly 30 of the aerosol provision system 10 of FIG. 1 in accordance with some embodiments. FIGS. 3-6 schematically represent the components represented in FIG. 2 at different stages of assembly of the heating element carrier module 160.

The carrier module 160 comprises a first carrier component (first part) 101 and a second carrier component (second part) 102. As described further below, these two components 101, 102 play a role in supporting the heating element 103, and in this regard may sometimes be referred to as providing a heating element cradle. Thus, the first and second components 101, 102 represented in FIG. 2 may for convenience, and having regard to the orientation represented in the figures, also be referred to as an upper cradle 101 and a lower cradle 102. However, it will be appreciated the terms "upper" and "lower", and similar orientation-related terms, are used herein purely for convenience in referring to elements represented in the accompanying figures and are not intended to indicate any particular orientation for these components is required for implementing the various embodiments described herein. The carrier module 160 further comprises the heating element 103 and a first electrical contact element 104 for connecting to a first end of the heating element 103 and a second electrical contact element 105 for connecting to a second end of the heating element 103.

The upper and lower cradle components 101, 102 in this example are molded from a plastics material having a high glass fiber content (e.g. 50%) to provide improved rigidity and resistance to high temperatures, for example temperatures around 230 degrees centigrade. The respective upper and lower cradle components 101, 102 are broadly speaking of a generally semi-circular cross-section (although with variations in size and shape along their lengths as discussed further below). Each cradle component is provided with a recess 120 (only visible for lower cradle component 102 in FIG. 2) running along its length on what would otherwise be their flattest faces so that when the two cradle components 101, 102 are brought together to sandwich the heating element 103 as discussed further below they form a cradle having a generally tubular configuration with an airflow path (defined by the respective recesses 120) running down the interior of the tube and in which the heating element 103 is disposed.

The first and second electrical contact elements 104, 105 may be formed of a sheet metal material, for example comprising copper strips formed into an appropriate shape having regard to the shape and configuration of the other elements of the apparatus in accordance with conventional manufacturing techniques. In other cases the first and second electrical contact elements 104, 105 may comprise conventional flexible wiring. In some examples the first and/or second electrical contact elements may be provided with plating, for example gold plating, to help lower contact resistance and/or reduce any risk of corrosion.

The heating element 103 is formed from a sintered metal fiber material and is generally in the form of a sheet. However, it will be appreciated that other porous conducting materials may equally be used. In this particular example the heating element 103 comprises a main portion 103A with electrical contact extensions 103B at each end for connecting to the respective electrical contact elements 104, 105. The overall resistance of the heating element 103 between the electrical contact extensions 103B in this example is around 1 ohm. However, it will be appreciated that other resistances may be selected, for example having regard to the available battery voltage and the desired temperature/power dissipation characteristics of the heating element 103. In this regard the relevant characteristics may be selected in accordance with the desired aerosol generation properties for the apparatus in accordance with the established principles of aerosol generation for the source liquid of interest. The main portion 103A of the heating element 103 is generally rectangular with a length (i.e. in a direction running between the electrical contact extensions 103B) of around 20 mm and a width of around 8 mm. The thickness of the sheet comprising the heating element 103 in this example is around 0.15 mm. As can be seen in FIG. 2, the generally-rectangular main portion 103A of the heating element 103 has slots extending inwardly from each of the longer sides. The slots extend inwardly by around 4.8 mm and have a width of around 0.6 mm. The slots extending inwardly are separated from one another by around 5.4 mm on each side of the heating element 103 with the slots extending inwardly from the opposing sides being offset from one another by around half this spacing. A consequence of this arrangement of slots in the heating element 103 is that current flow along the heating element 103 is in effect forced to follow a meandering path which results in a concentration of current, and hence electrical power, around the ends of the slots. The different current/power densities at different locations on the heating element 103 mean there are areas of relatively high current density that become hotter than areas of relatively low current density. This in effect provides the heating element with a range of different temperatures and increases temperature gradients, which can be desirable in the context of aerosol provision systems. This is because different components of a source liquid may aerosolize/vaporize at different temperatures and so providing a heating element with a range of temperatures can help simultaneously aerosolize a range of different components in the source liquid.

A process of assembling the components represented in FIG. 2 to provide a heating element carrier module 160 for use in a cartridge assembly 30 of an electronic cigarette 10 in accordance with certain embodiments is now described with reference to FIGS. 3 to 6.

Figure 3:
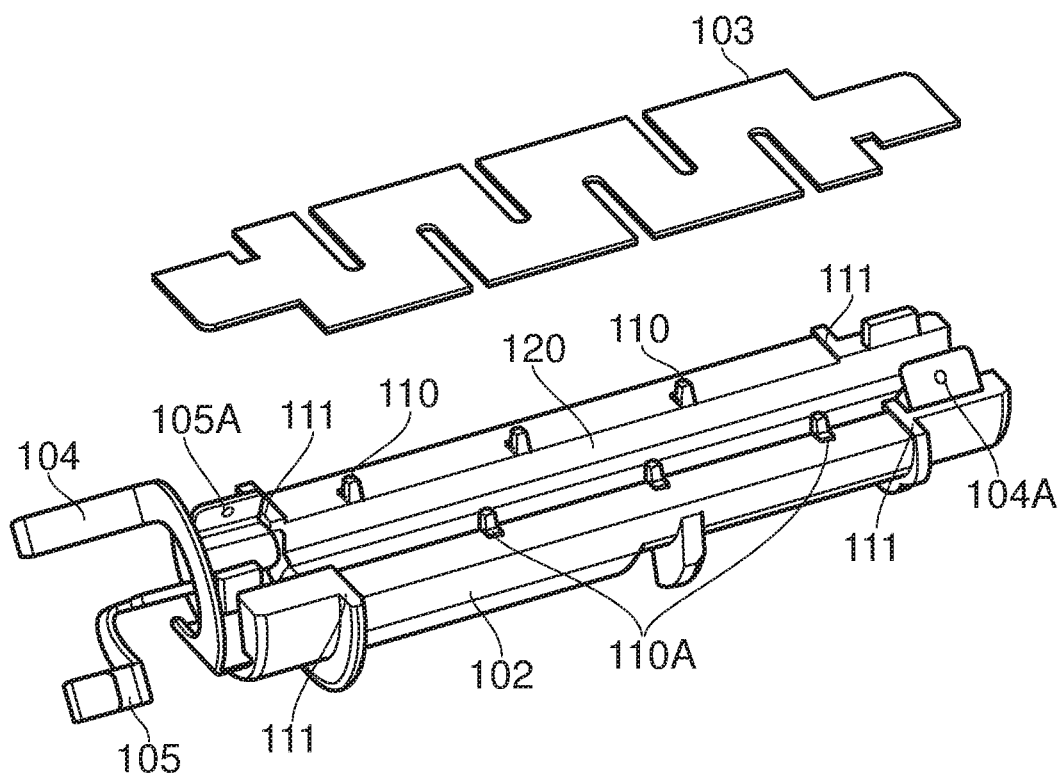
FIGS. 3 to 6 schematically represent the components represented in FIG. 2 at different stages of assembly of a heating element carrier module for use in a cartridge assembly in accordance with some embodiments.

As can be seen in FIG. 3, the first and second electrical contact elements 104, 105 have been mounted to the lower cradle component 102 and the heating element 103 is represented above the lower cradle component 102 ready to be put in place. The second electrical contact element 105 is mounted at a second end of the lower cradle component 102 (the leftmost end for the orientation in FIG. 3). The lower cradle component 102 is profiled to receive and match the shape of a first portion of the second electrical contact element 105 in accordance with conventional manufacturing techniques for mounting electrical conductors to plastic body parts. One end of the second electrical contact element 105 provides a second electrical contact element clamp portion 105A for receiving one of the electrical contact extensions 103B of the heating element 103 while the other end of the second electrical contact element 105 extends away from the lower cradle component 102 as schematically represented in the figure. The first electrical contact element 104 is mounted so as to run along the length of the lower cradle component 102 adjacent a wall of the recess 120. As for the second electrical contact element 105, one end of the first electrical contact element 104 extends away from the second end of the lower cradle component 102 as schematically represented in the figure. The other end of the first electrical contact element 104 provides a first electrical contact element clamp portion 105A arranged at a first end of the lower cradle component 102 (rightmost end in FIG. 3) for receiving the other of the electrical contact extensions 103B of the heating element 103.

As can be seen in FIG. 3, an upper surface of the lower cradle component 102 comprises a plurality of locating pegs 110 which align with the slots in the heating element 103 discussed above and corresponding locating holes in the upper cradle 101 (not shown in the figures). These locating pegs 110 are for helping to align the upper cradle 101 with the lower cradle 102, and for helping to align the heating element 103 relative to the upper and lower cradles 102 when assembled.

Figure 4:
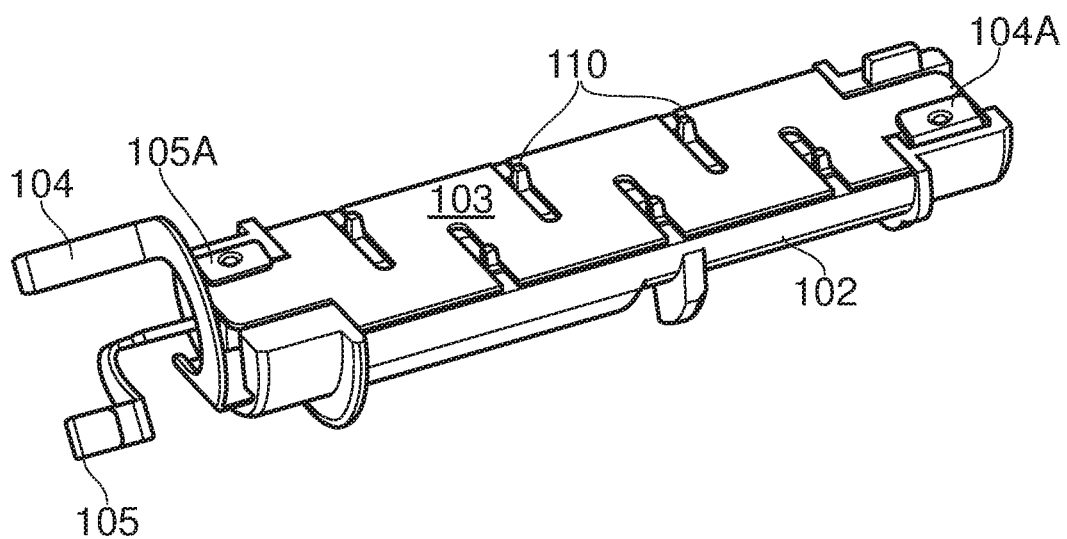

FIG. 4 schematically shows the heating element 103 mounted to the lower cradle 102 containing the first and second electrical contact elements 104, 105. The heating element 103 is mounted to the lower cradle 102 simply by being placed on the upper surface of the lower cradle 102 with the locating pegs 110 aligned with the slots of the heating element 103. Slightly raised portions of the upper surface of the lower cradle element 102 provide locating walls 111 in the vicinity of the electrical contact extensions 103B at each end of the heating element 103 to further help align the heating element 103. In this example, the locating walls 111 are separated by slightly more than the size of the heating element 103 and the locating pegs 110 are slightly smaller than the size of the slots so the heating element 103 is overall free to move slightly in the horizontal plane, for example by around 0.1 mm. This is to allow for thermal expansion and contraction when the heating element 103 is in use to help avoid buckling. The first and second electrical contact element clamping portions 104A, 105A are bent down so as to clamp around respective ones of the electrical contact extensions 103B at each end of the heating element 103, thus providing an electrical connection between the portions of the electrical contact elements 104, 105 extending away from the lower cradle component 102 and the ends of the heating element 103. In this example the electrical connections between the electrical contact elements 104, 105 and the heating element 103 rely solely on physical contact, but in other implementations other techniques may be used, for example welding or soldering.

Figure 5:
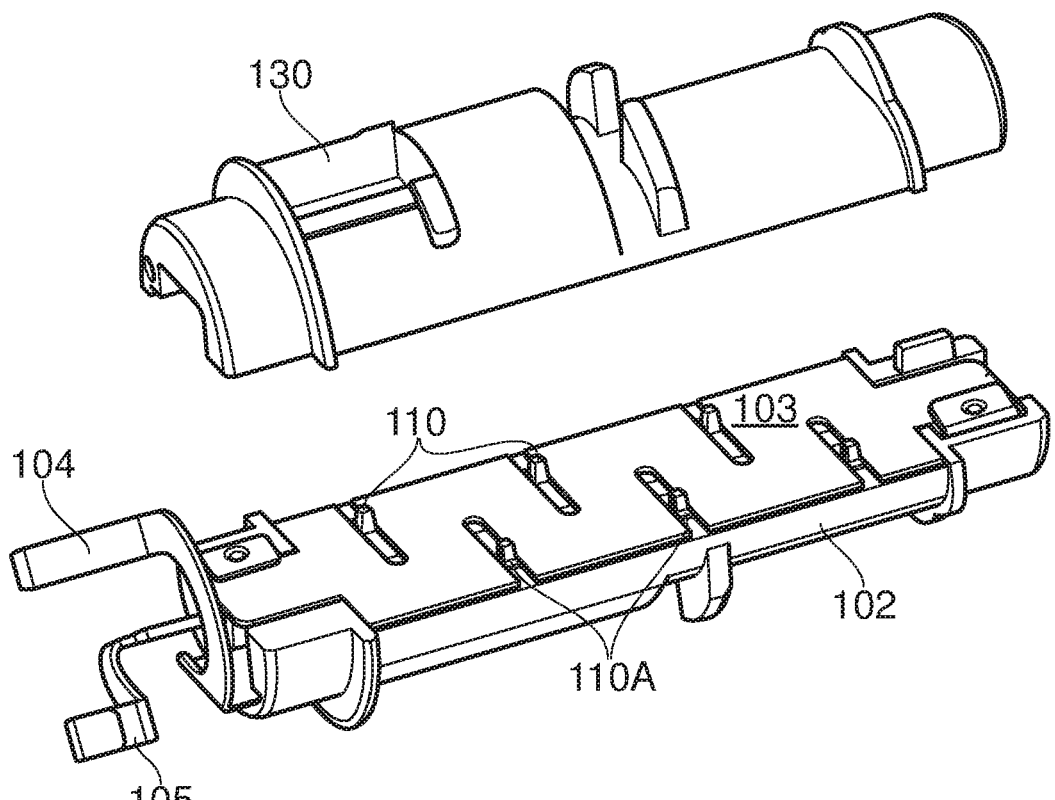

FIG. 5 schematically shows the combined lower cradle component 102, first and second electrical contact elements 104, 105 and the heating element 103 as represented in FIG. 4, but with the other cradle component 101 shown ready to be mounted to the lower cradle component 102.

Figure 6:
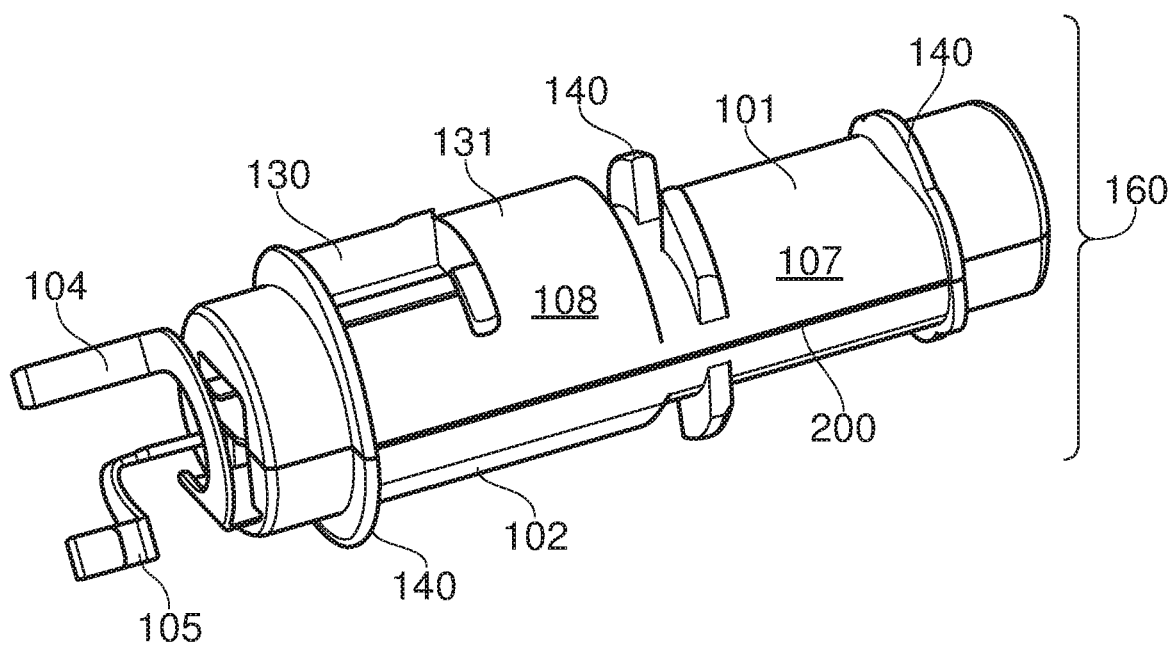

FIG. 6 schematically shows the upper cradle component 101 mounted to the lower cradle component 102 (and other elements represented in FIG. 4) to provide an assembled carrier module 160. The upper cradle component 101 is mounted to the lower cradle component 102 by simply placing them together with the locating pegs 110 of the lower cradle component 102 aligned with corresponding locating holes (not shown) in the upper cradle component 101. As can be seen in FIGS. 4 and 5, the locating pegs 110 are each provided with a shoulder 110A. The shoulders 110A have a height above the upper surface of the lower cradle component 102 of around 0.18 mm (i.e. 0.03 millimeters larger than the thickness of the heating element), and this also matches the height of the locating walls 111. The shoulders 110A are sized and arranged so as to fall within the slots of the heating element 103. However, the corresponding locating holes in the upper cradle component 101 are sized only to receive the locating pegs 110, and not their shoulders. Thus, when the upper cradle component 101 is mounted to the lower cradle component 102 they are separated by a gap corresponding to the height of the shoulders 110A and the locating walls 111. Because this gap between the upper and lower cradle components 101, 102 is 0.18 mm, and the heating element 103 has a thickness of 0.15 mm, the heating element 103 is loosely sandwiched between the upper and lower cradle components 101, 102, rather than being fixedly clamped in place. As noted above, this loose mounting of the heating element 103 is to allow for thermal expansion and contraction of the heating element 103 during use.

Thus the assembled carrier module 160 is generally tubular with a central passageway defined by the respective recesses 120 in the upper and lower carrier components 101, 102 providing an airflow path through the carrier module 160. In this example the airflow path defined by the upper and lower carrier components 101, 102 has a generally rectangular cross-section with a width of around 4 mm and a height of around 2.2 mm and with the heating element 103 being disposed in a plane around the middle of the airflow path. The carrier module 160 has an overall length of around 2.5 cm and a diameter of around 1 cm at its widest. The outer surface of the carrier module 160 (provided by the respective outer surfaces of the first and second cradle components 101, 102) comprises various surface profile features. Most notably, the carrier module 160 comprises a first portion 107 arranged towards one end of the carrier module 160 (rightmost in FIG. 6) which has a cross-sectional area that is smaller than that of a second portion 108 arranged towards the other end of the carrier module 160 (leftmost in FIG. 6). The first and second portions 107, 108 of the carrier module 160 have broadly the same width in the plane of the heating element 103 (i.e. at the interface between the upper and lower cradle components 101, 102), but different thicknesses in a direction perpendicular to the plane of the heating element 103. Thus the larger second portion 108 has a generally circular cross-section whilst the smaller first portion 101 has a generally elongate cross-section (see FIG. 11 discussed further below). Thus, there is a step change in the cross-sectional area of the carrier module 160 around halfway along its length. The outer surface of the carrier module 160 further comprises a number of protrusions 140, a chamber 130 defined by a recess in the larger second portion 108 of the carrier module 160, and flat region 131 on the outer surface of the larger second portion 108 of the carrier module 160 extending from the chamber 130 to where the larger second portion 108 of the carrier module 160 meets the smaller first portion 107 of the carrier module 160. Although not apparent in FIG. 6, the upper cradle component 101 also comprises a passageway connecting between the flow path 120 running through the interior of the carrier module 160 and the chamber 130. These features may be molded into the respective cradle components 101, 102 during their manufacture and the respective functions of these various elements are discussed further below.

Figure 7:
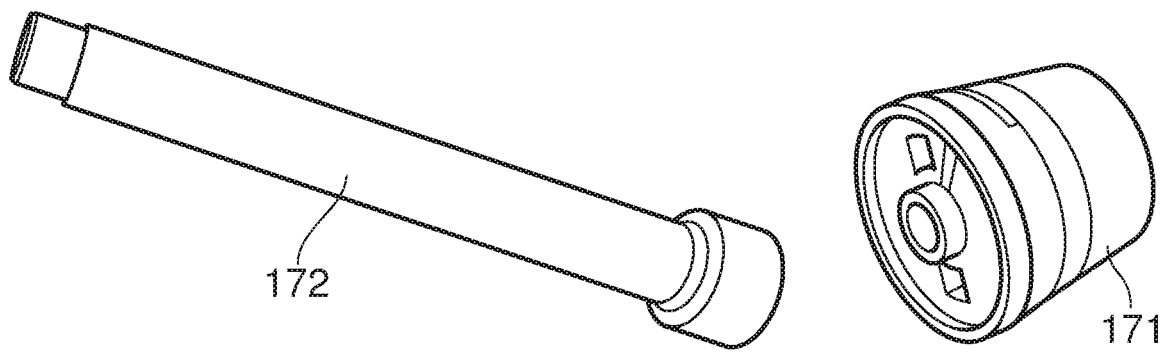
FIG. 7 schematically represents some further components of a cartridge assembly in accordance with some embodiments.
Figure 7:
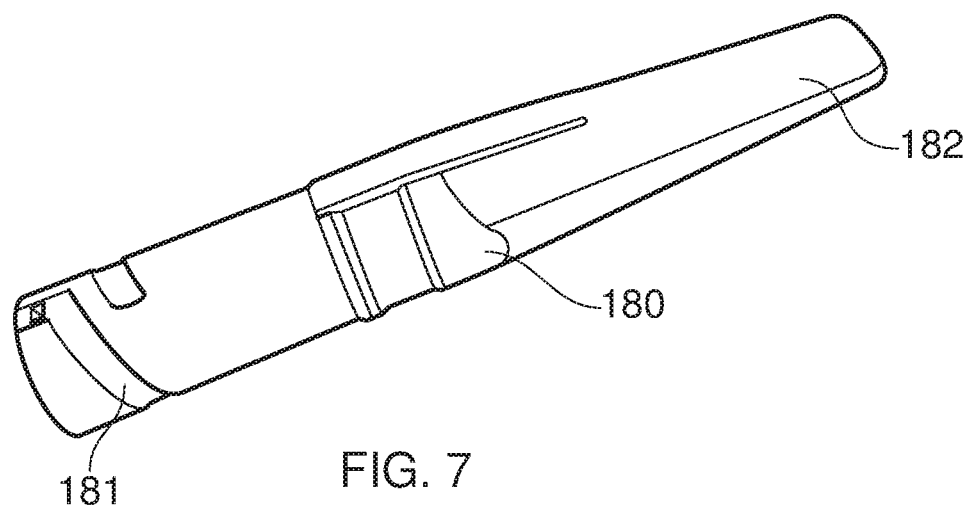

FIG. 7 schematically represents some further components of a cartridge assembly 30 comprising the carrier module 160 of FIG. 6 in accordance with certain embodiments. More specifically, FIG. 7 shows a first sealing element (sealing ring) 171, a second sealing element in the form of a support tube 172, and an outer housing 180 for the cartridge assembly 30. These components may be molded from plastics material, for example polypropylene.

Figure 8:
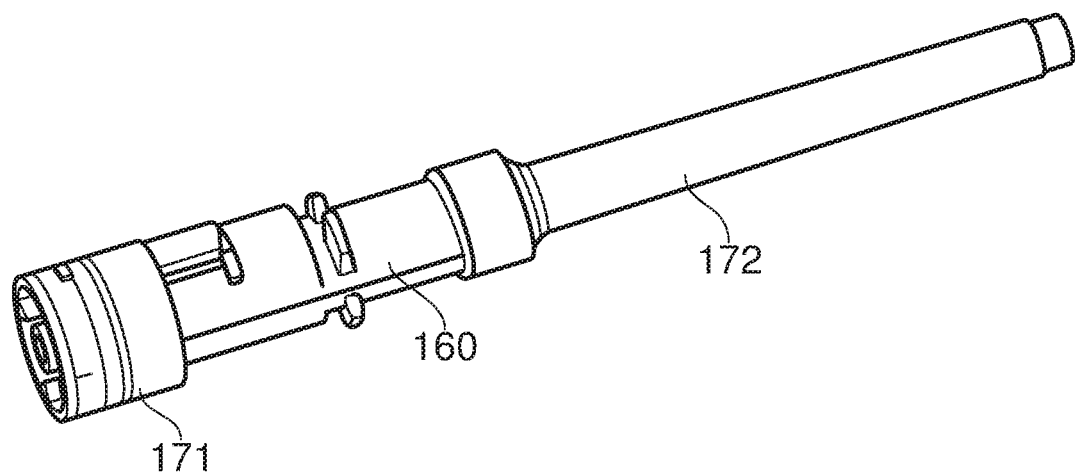
FIGS. 8 to 10 schematically represents a cartridge assembly comprising the heating element carrier module of FIG. 6 and the further components of FIG. 7 at different stages of assembly in accordance with some embodiments.

FIG. 8 schematically represents how the first and second sealing elements 171, 172 are mounted to the carrier module 160.

The first sealing element 171 comprises a recess for receiving the second end (leftmost in FIG. 8) of the carrier module 160. The recess in the first sealing element 171 is sized to receive the portion of the carrier module 160 which is to the left of the leftmost protrusion 140 seen in FIG. 6 and to above against this protrusion. The first sealing element 171 may be fixed to the carrier module 160 by a friction and/or snap fitting. The first sealing ring 171 further comprises openings through which the respective parts of the first and second electrical contact elements 104, 105 that extend away from the carrier module 160 pass, thereby allowing electrical contact with the heater 103 to be established through the first sealing ring 171 via the respective electrical contact elements 104, 105. The first sealing element 171 furthermore comprises a central opening in alignment with the airflow path through the carrier module 160. This central opening may be provided with an airflow deflector element arranged to help direct air being drawn into the carrier module 160 to either side of the heating element 103.

The second sealing element (support tube) 172 comprises a recess for receiving the first end (rightmost in FIG. 8) of the carrier module 160. The recess in the second sealing element 172 is sized to receive the portion of the carrier module 160 which is to the right of the rightmost protrusion 140 seen in FIG. 6 and to abut against this protrusion. The second sealing element 172 may also be fixed to the carrier module 160 by a friction and/or snap fitting. The second sealing element 172 is hollow with a central opening providing an extension to the airflow path through the carrier module 160.

Figure 9:
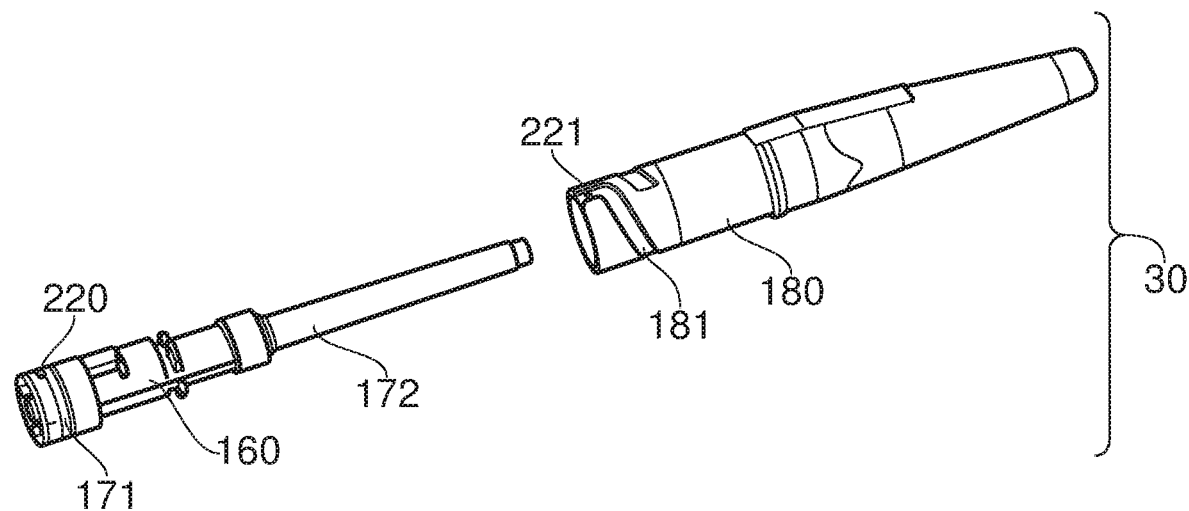
Figure 10:
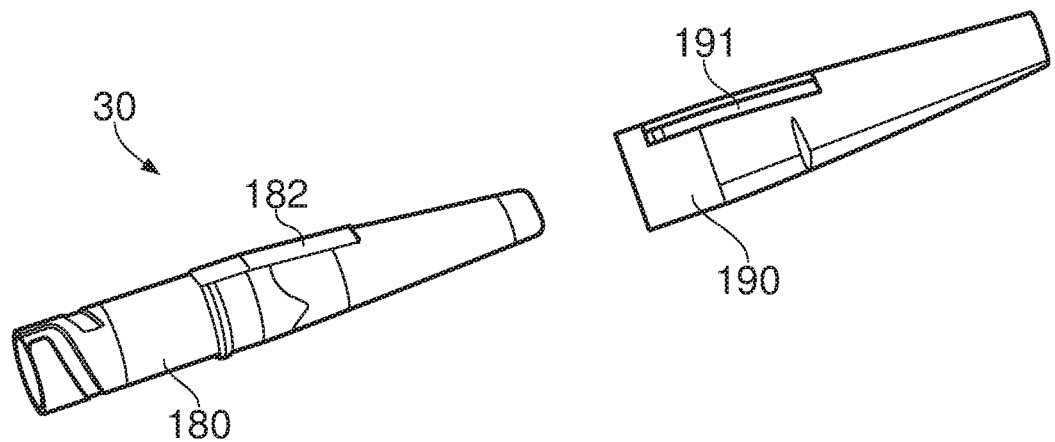

FIG. 9 schematically shows the combined sealing ring 171, carrier module 160 and support tube 172 ready for insertion into the outer housing 180. The combined carrier module 160 and sealing elements 171, 172 may thus be simply inserted into the outer housing 180 to provide a cartridge assembly 30 as schematically represented in FIG. 10. Also shown in FIG. 10 is a mouthpiece cover 190 which may be placed over a portion of the outer housing 180. The outer housing 180 has a raised portion 182 which matches a correspondingly sized opening 191 in the mouthpiece cover 190 to provide a snap fitting engagement for locating the mouthpiece cover 190 on the outer housing 180 to help locate the mouthpiece cover 190 on the outer housing 180. The mouthpiece cover 190 may be provided for aesthetic and/or hygiene reasons, and may further be provided with a surface texture, e.g. a rubberized texture, to provide what users may perceive to be a more pleasing feel than bare plastic. The raised portion 182 may be transparent to allow the interior of the outer housing 180 to be viewed, for example to ascertain a fill level for the cartridge assembly 30.

The rightmost end of the support tube 172 is received in a correspondingly sized recess at the rightmost end of the outer housing 180. The sealing ring 171 is received in the leftmost end of the outer housing 180. A compliant seal around the sealing ring 171 forms a seal with the inner surface of the outer housing 180. The combined sealing elements 171, 172 and carrier module 160 may be fitted into the outer housing 180 with a snap and/or friction fitting. For example, the sealing ring 171 in this example is provided with a protrusion 220 that is received in an opening in the inner wall of the outer housing 180 to provide a snap fitting. The protrusions 140 on the carrier module 160 mentioned above are sized so as to abut against the interior wall of the outer housing 180 when the carrier module 106 is inserted into the outer housing 180 so as to hold the carrier module 160 in place relative to the outer housing 180. The outer housing 180 has a generally cylindrical portion surrounding the carrier module 160 and a generally tapering portion surrounding the support tube 172. The outer housing 180 has a generally uniform wall thickness such that there is a relatively small gap between the larger second portion 108 of the carrier module 160 and the inner wall of the outer housing 180, e.g. around 0.5 mm or less, and a relatively large gap between the smaller first portion 107 of the carrier module 160 and the inner wall of the outer housing 180. There is a tapering gap provided between the support tube 172 and the inner wall of the tapering portion of the other housing 180 which reduces down towards where the end of the support tube 172 is received at the end of the outer housing 180.

The space between the outer wall of the carrier module 160 and the inner wall of the outer housing 180 defines at least a part of the source liquid reservoir 38 for the cartridge assembly 30. In this example the reservoir 38 for the source liquid further comprises the gap between the support tube 172 and the inner wall of the tapering portion of the outer housing 180. This reservoir 38 may be filled with source liquid through an opening (not shown) in the outer housing 180 which is sealed after filling, e.g. by plugging.

The leftmost end of the cartridge assembly 30 comprises an engagement mechanism for removeably engaging the cartridge 30 to a body portion 20 of an electronic aerosol provision system with which the cartridge assembly 30 is connected in normal use. In this example the engagement mechanism comprises a partial (e.g. less than one turn) female screw thread for cooperating with a corresponding male screw thread on the body portion 20 of the electronic aerosol provision system with which the cartridge assembly 30 is intended to be used. Other engagement mechanisms, for example based around bayonet, friction or snap fitting could be used in other implementations. The body portion 20 of an electronic aerosol prison system with which the cartridge assembly 30 is intended to be used is provided with electrical connectors for cooperating with the portions of the first and second electrical contact elements 104, 105 extending through the sealing element 171 to establish an electrical connection between the heater 103 and the body portion 20. This may be achieved in accordance with conventional techniques for standard electrical connections between removable elements, for example using spring-loaded collector pins.

Figure 11:
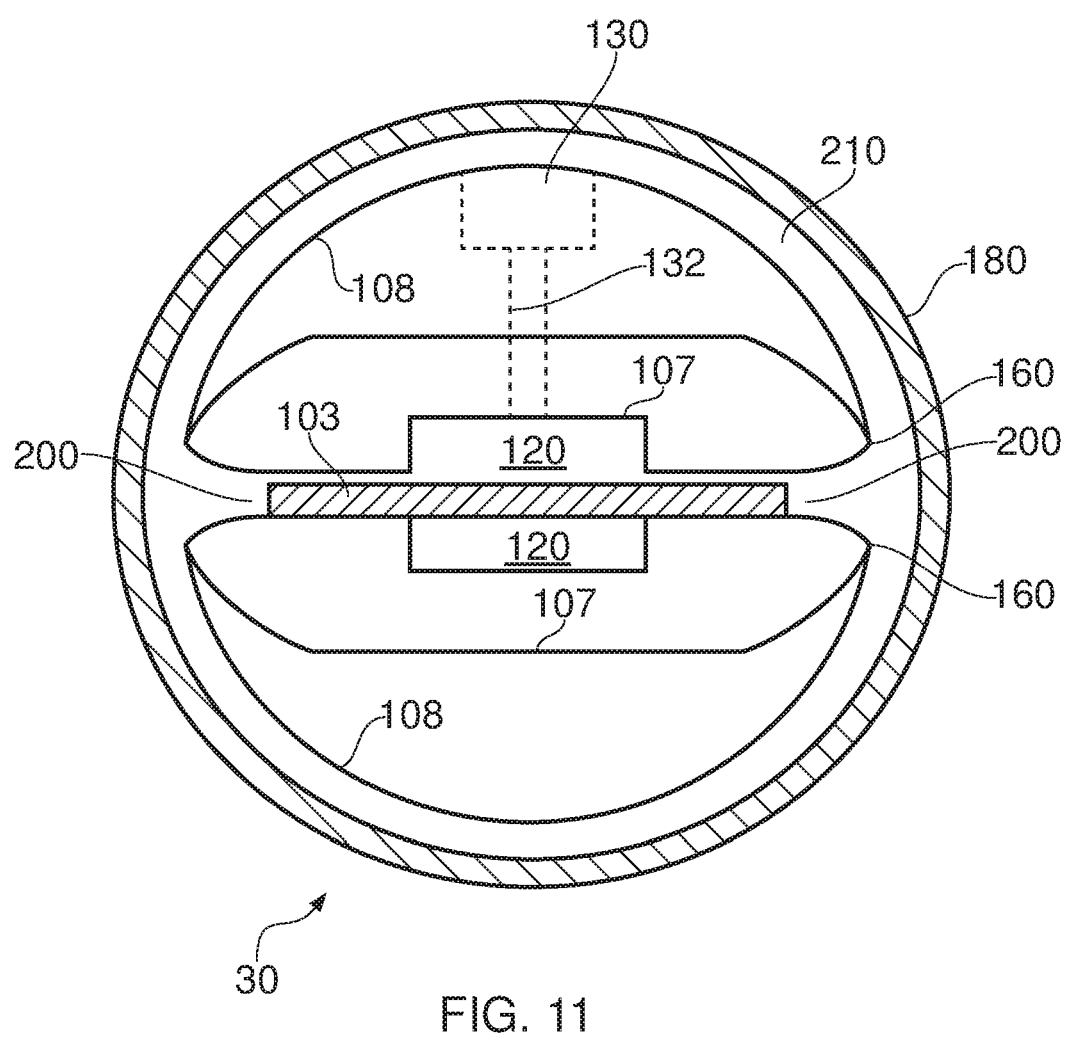
FIG. 11 schematically represent a cross-section through a cartridge assembly in accordance with an embodiment.

FIG. 11 schematically represents some aspects of the cartridge assembly 30 represented in FIG. 10 in schematic cross-section. The cross-section is taken through a section of the first portion 107 of the carrier module 160 (i.e. the smaller/thinner portion) in a plane perpendicular to the airflow path 120 (i.e. perpendicular to the direction along which airflows in the airflow path when the apparatus is in normal use). The cross-section represented in FIG. 11 is not a strict cross-section in that the figure also schematically represents further aspects of the cartridge assembly 30 which are not in the plane of the cross-section. In particular, the figure also represents the outer periphery of the second (larger/fatter) portion of the carrier module 160 as well as the chamber 130 in this portion of the carrier module 160 and passageway 132 connecting between this chamber 130 and the airflow path 120 (the chamber 130 and passageway 132 are represented by dotted lines). As described above the upper and lower cradle component 101, 102 are configured to engage in such a way as to define a gap in which the heater 103 is arranged (the gap preferably being slightly larger than the thickness of the heater 103). This gap is in fluid communication with the space between the outer wall of the carrier module 160 and the inner wall of the outer housing 180 which together define (a part of) the reservoir 38 for source liquid.

Thus, the gap between the upper and lower cradle components 101, 102 provides capillary channels 200 which extend along both sides of the heating element 103 and through which source liquid may be drawn from the reservoir 38 to the heating element 103 for vaporization to generate an aerosol in the airflow path 120 during use. The aerosol generated at the heater 103 may then be drawn along the airflow path 120 and through the support tube 172 to exit the cartridge assembly 30 through the mouthpiece end of the outer housing 180 (i.e. the part covered by the mouthpiece cover 190) as a user inhales on the electronic cigarette 10 comprising the cartridge assembly 30.

The passageway 132 providing fluid communication between the airflow path 120 and the reservoir 38 defined by the space between the carrier module 160 and the outer housing 180 allows for air to enter the reservoir 38 from the airflow path 120 to replace source liquid that has been drawn through the capillary gap 200 and vaporized (i.e. the passageway 132 allows for pressure balancing/air ventilation between the airflow path 120 and the reservoir 38 of source liquid). The chamber 130 is provided to allow source liquid to temporarily accumulate in this region during a puff of the reservoir 38. The inventors have found this configuration reduces the chance of source liquid leaking into the airflow path 120 through the passageway 132. The flat region 131 connecting between the chamber 130 and the portion of the reservoir 38 adjacent the thinner part 107 of the carrier module 160 (see FIG. 6) has been found to help ensure that air passes from the chamber 130 into the main body of the reservoir 38 adjacent the first portion 107 of the carrier module 160 rather than becoming stuck in the thinner part of the reservoir 38 between the larger portion 108 of the carrier module 160 and the outer housing 180.

Thus, certain embodiments provide an apparatus (e.g. a cartridge assembly) for an electronic aerosol provision system (e.g. electronic cigarette). The cartridge assembly comprises a reservoir 38 for a source liquid and a carrier module that defines an airflow path 120 within the reservoir 38 and comprises a heating element 103 supported in the airflow path. The carrier module 160 comprises a first part (upper cradle component) 101 and a second part (lower cradle component) 102 which cooperatively engage to support the heating element 103 with a gap between the first part and second parts providing capillary channels 200 arranged to draw source liquid to the heating element 103 from the reservoir 38.

The inventors have found this to be a configuration which provides an effective supply of source liquid to the heating element 103 without giving rise to problems with leakage.

As described above, the upper and lower cradle components 101, 102 cooperatively engage at an interface which extends in a direction that is substantially parallel to a direction along which air flows in the airflow path when the apparatus is in normal use. By in effect splitting the holder (cradle) and arranging the heating element 103 in the plane of the interface between the two parts of the holder, the heating element 103 can be supported around a relatively large fraction of its periphery, and this can be helpful because of the relatively fragile nature of the heating elements 103. Furthermore, the two-part configuration has been found to aid manufacturing and assembly, whilst providing a ready mechanism for defining appropriately sized capillary gaps for drawing source liquid to the heating element 103 from the surrounding reservoir 38.

As can be seen in FIG. 11, the upper and lower cradle portions 101, 102 are provided with rounded corners such that the gap between them defining the capillary gap increases with increasing distance from the airflow path 120. The inventors have found this further helps maintain an appropriate supply of source liquid to the heater 103 during use. However, in other example embodiments the capillary gap might not increase in width and maintain the same width out to the edges of the upper and lower cradle parts 101, 102.

As noted above, the space between the carrier module 160 and the outer housing 180 along a first (thinner) portion 107 of the carrier module 160 is larger than the space between the carrier module 160 and the outer housing 180 along a second portion (fatter) portion of the carrier module 160. This approach has been found to help with maintaining an appropriate supply of source liquid to the heating element 103 for different orientations of the cartridge assembly 30 while still allowing for a reasonable reservoir capacity. This is because the space between the carrier module 160 and the outer housing 180 along the first portion of the carrier module 160 defines a main body of the reservoir 38 for storing the majority of the source liquid that is around the airflow path to provide reasonable capacity. However, the space between the carrier module 160 and the outer housing 180 along the second (fatter) portion of the carrier module 160 is sized so as to define an annular capillary space 210 extending around the carrier module 160 along the second portion of the carrier module 160. This annular capillary space 210 can in effect store source liquid to be drawn to the heating element 103 regardless of the orientation of the cartridge assembly 30.

It will be appreciated there are various modifications to the configurations described above which may be adopted in accordance with other embodiments.

For example, whereas in the above implementation a gap is provided on both sides of the heating element 103, in some configurations one side of the heating element 103 may be blocked, such that only a single capillary channel is provided to supply source liquid to the heating element 103.

Furthermore, whereas in the example implementation represented in FIG. 11 the heating element 103 is contained within the capillary gap 200, in some other example implementations, the heating element 103 may extend beyond the capillary gap 200 and into the reservoir 38.

Furthermore, whereas in the example implementations described above the carrier module 160 has been provided with protrusions 140 to help locate the carrier module 160 within the outer housing 180, in other implementations the inner wall of the outer housing 180 may instead, or in addition, be provided with protrusions for this purpose.

In some implementations the chamber 130 may not be provided so the air passage 132 seen in FIG. 11 would in effect be extended out to the outer surface of the cradle component in which the passage way 132 is provided (i.e. the upper cradle component 101 in the example represented FIG. 11).

Furthermore, whereas in the above-described examples the flat region 131 extends directly in a straight line from the chamber 130 to the main body of the reservoir 38 adjacent the first portion 107, in another implementation the flat region 131 may instead follow a non-straight path from the chamber 130 (or the end of the passageway 132 in the event there is no chamber) to the main body of the reservoir 38. This may be so as to increase the overall length of the flat region 131, thereby increasing its effective resistance to fluid flow. In yet other examples, the flat region 131 may be replaced by a groove formed in the outer surface of the cradle component, and this may be straight or follow a meandering path to increase its flow resistance.

In yet other example implementations, there may be no passage way 132 (and no chamber 130; and no groove or flat region 131). Instead, pressure balancing between the airflow path 120 and the reservoir 38 may be provided by air flowing in the parts of the very gaps which are not occupied by the heating element 103 (because the gap may be wider than the thickness of the heating element 131).

Thus there has been described an apparatus for an electronic aerosol provision system. The apparatus may comprise a replaceable cartridge for the electronic aerosol provision system or may comprise a fixed component of a re-fillable or disposable electronic aerosol provision system. The apparatus comprises a reservoir for a source liquid and a carrier module supported within the reservoir. The carrier module defines an airflow path within the reservoir and comprises a heating element supported in the airflow path for generating an aerosol from the source liquid and first and second mounting parts which cooperatively engage to support the heating element. The first and second mounting parts of the carrier module cooperatively engage at an interface which extends in a direction that is substantially parallel to a direction along which air flows in the airflow path when the apparatus is in normal use. A gap between the first and second mounting parts may provide a capillary channel for drawing source liquid to the heating element from the reservoir heating during use.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. An apparatus for an electronic aerosol provision system comprising:
   a reservoir for a source liquid; and
   a carrier module that defines an airflow path within the reservoir and comprises a heating element supported in the airflow path within the reservoir for generating an aerosol from the source liquid, wherein the carrier module comprises a first part and a second part which cooperatively engage to support the heating element, wherein the first part and the second part of the carrier module cooperatively engage at an interface which extends in a direction that is substantially parallel to a direction along which air flows in the airflow path when the apparatus is in normal use, and wherein the heating element comprises a sheet material extending in a plane which is substantially parallel to the interface between the first part and the second part, and wherein a gap between the first part and second part provides a capillary channel arranged to draw source liquid to the heating element from the reservoir, wherein a width of the gap between the first part and second part of the carrier module increases with increasing distance from the airflow path.

2. The apparatus of claim 1, wherein a peripheral part of the heating element is received in the gap between the first part and second part to thereby support the heating element in the airflow path.

3. The apparatus of claim 1, wherein at least one of the first part and the second part of the carrier module comprises one or more locating pegs received in corresponding locating holes of the other of the first part and the second part of the carrier module so as to help maintain their relative alignment.

4. The apparatus of claim 1, wherein the heating element comprises a sintered metal fiber material.

5. The apparatus of claim 1, wherein the heating element is supported loosely with respect to the first and second parts of the carrier module.

6. The apparatus of claim 1, wherein the arrangement of the airflow path within the reservoir is such that the reservoir is around the airflow path, the apparatus further comprising an outer housing in which the carrier module is received such that the reservoir around the airflow path is defined at least in part by a space between the carrier module and the outer housing.

7. The apparatus of claim 6, further comprising one or more spacer elements arranged to support the carrier module at a defined position within the outer housing.

8. The apparatus of claim 7, wherein the one or more spacer elements comprise one or more protrusions formed on an outer surface of at least one of the first or second parts of the carrier module.

9. The apparatus of claim 7, wherein the one or more spacer elements comprise one or more protrusions formed on an inner surface of the outer housing.

10. The apparatus of claim 6, further comprising a first sealing element for providing a seal between the carrier module and the outer housing at one end of the carrier module and a second sealing element for providing a seal between the carrier module and the outer housing at another end of the carrier module.

11. The apparatus of claim 10, wherein the first sealing element comprises a sealing ring arranged between the carrier module and the outer housing.

12. The apparatus of claim 6, wherein the space between the carrier module and the outer housing along a first portion of the carrier module is larger than the space between the carrier module and the outer housing along a second portion of the carrier module.

13. The apparatus of claim 12, wherein the space between the carrier module and the outer housing along the first portion of the carrier module defines a main body of the reservoir for storing a majority of source liquid that is around the airflow path.

14. The apparatus of claim 12, wherein the space between the carrier module and the outer housing along the second portion of the carrier module defines a capillary space extending around the carrier module along the second portion of the carrier module.

15. An apparatus for an electronic aerosol provision system comprising:

a reservoir for a source liquid; and a carrier module that defines an airflow path within the reservoir and comprises a heating element supported in the airflow path within the reservoir for generating an aerosol from the source liquid, wherein the carrier module comprises a first part and a second part which cooperatively engage to support the heating element, wherein the first part and the second part of the carrier module cooperatively engage at an interface which extends in a direction that is substantially parallel to a direction along which air flows in the airflow path when the apparatus is in normal use, and wherein the heating element comprises a sheet material extending in a plane which is substantially parallel to the interface between the first part and the second part, and wherein a gap between the first part and second part provides a capillary channel arranged to draw source liquid to the heating element from the reservoir, wherein at least one of the first part and the second part of the carrier module comprises one or more locating pegs received in corresponding locating holes of the other of the first part and the second part of the carrier module so as to help maintain their relative alignment, and wherein the one or more locating pegs pass through one or more corresponding openings in the heating element so as to help maintain the heating element in position relative to the first and second parts of the carrier module.

16. An apparatus for an electronic aerosol provision system comprising:
  a reservoir for a source liquid; and
  a carrier module that defines an airflow path within the reservoir and comprises a heating element supported in the airflow path within the reservoir for generating an aerosol from the source liquid, wherein the carrier module comprises a first part and a second part which cooperatively engage to support the heating element, wherein the first part and the second part of the carrier module cooperatively engage at an interface which extends in a direction that is substantially parallel to a direction along which air flows in the airflow path when the apparatus is in normal use, and wherein the heating element comprises a sheet material extending in a plane which is substantially parallel to the interface between the first part and the second part, and wherein a gap between the first part and second part provides a capillary channel arranged to draw source liquid to the heating element from the reservoir,
  wherein the arrangement of the airflow path within the reservoir is such that the reservoir is around the airflow path, the apparatus further comprising an outer housing in which the carrier module is received such that the reservoir around the airflow path is defined at least in part by a space between the carrier module and the outer housing,
  wherein the apparatus further comprises a first sealing element for providing a seal between the carrier module and the outer housing at one end of the carrier module and a second sealing element for providing a seal between the carrier module and the outer housing at another end of the carrier module, and
  wherein the second sealing element comprises a support tube providing an extension to the air flow path and having a first end coupled to the carrier module and a second end coupled to an aerosol outlet end of the outer housing.

17. An apparatus for an electronic aerosol provision system comprising:
  a reservoir for a source liquid; and
  a carrier module that defines an airflow path within the reservoir and comprises a heating element supported in the airflow path within the reservoir for generating an aerosol from the source liquid, wherein the carrier module comprises a first part and a second part which cooperatively engage to support the heating element, wherein the first part and the second part of the carrier module cooperatively engage at an interface which extends in a direction that is substantially parallel to a direction along which air flows in the airflow path when the apparatus is in normal use, and wherein the heating element comprises a sheet material extending in a plane which is substantially parallel to the interface between the first part and the second part. and wherein a gap between the first part and second part provides a capillary channel arranged to draw source liquid to the heating element from the reservoir,
  wherein at least one of the first and second parts of the carrier module is provided with a passageway to allow air to pass between the flow path and the reservoir.

\* \* \* \* \*